US009814871B2

United States Patent
Wlodarczyk et al.

(10) Patent No.: US 9,814,871 B2
(45) Date of Patent: Nov. 14, 2017

(54) CONNECTOR ASSEMBLY FOR SYRINGE SYSTEM

(71) Applicant: MEDRAD, INC., Indianola, PA (US)

(72) Inventors: Jaroslaw Wlodarczyk, Lower Burrell, PA (US); Edward P Liscio, Murrysville, PA (US); Arthur E Uber, III, Pittsburgh, PA (US); Kevin P Cowan, Allison Park, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 838 days.

(21) Appl. No.: 13/835,522

(22) Filed: Mar. 15, 2013

(65) Prior Publication Data

US 2014/0261758 A1    Sep. 18, 2014

(51) Int. Cl.
*A61M 39/10*    (2006.01)
*A61M 5/00*    (2006.01)
(Continued)

(52) U.S. Cl.
CPC ............ *A61M 39/10* (2013.01); *A61M 5/007* (2013.01); *A61M 5/14566* (2013.01);
(Continued)

(58) Field of Classification Search
CPC .......... A61M 39/10; A61M 2039/1027; A61M 5/1407; A61M 5/1408; A61M 5/1409;
(Continued)

(56) References Cited

U.S. PATENT DOCUMENTS 798,093 A    8/1905    Dean
817,054 A    4/1906    Gay
(Continued)

FOREIGN PATENT DOCUMENTS

EP    2005934 A2    12/2008
WO    9528195 A1    10/1995
(Continued)

OTHER PUBLICATIONS

The International Search Report and Written Opinion dated Jul. 30, 2014 from corresponding PCT Application No. PCT/US2014/022629.

(Continued)

*Primary Examiner* — Imani Hayman
*Assistant Examiner* — Nilay Shah
(74) *Attorney, Agent, or Firm* — Joseph L. Kent; David Schramm; James R. Stevenson

(57) ABSTRACT

A connector assembly for a fluid delivery system includes a conical body defining an interior cavity and a discharge outlet, the discharge outlet defining an internal passage in fluid communication with the interior cavity; and a connector removably attached to the discharge outlet. The connector includes a central body configured to be at least partially positioned within the internal passage of the discharge outlet, and an annular connector portion connected to the central body and configured to releasably engage an exterior of the discharge outlet, the central body defining an internal channel within the central body that is in fluid communication with the interior cavity of the conical body when the connector is attached to the discharge outlet.

13 Claims, 15 Drawing Sheets

(51) Int. Cl.
  *A61M 5/145* (2006.01)
  *A61M 5/14* (2006.01)
  *A61M 5/34* (2006.01)
  *A61M 5/32* (2006.01)
  *A61M 5/168* (2006.01)

(52) U.S. Cl.
  CPC ......... *A61M 5/1407* (2013.01); *A61M 5/1408* (2013.01); *A61M 5/16827* (2013.01); *A61M 5/348* (2013.01); *A61M 2005/3246* (2013.01); *A61M 2039/1016* (2013.01); *A61M 2039/1027* (2013.01); *Y10T 137/598* (2015.04)

(58) Field of Classification Search
  CPC .......... A61M 5/178; A61M 2039/1077; A61M 39/1011; A61M 39/20; A61M 2039/1016; A61M 2039/1044; A61M 2039/1094
  See application file for complete search history.

(56) References Cited

U.S. PATENT DOCUMENTS

| | | | |
|---|---|---|---|
| 1,388,946 A | 8/1921 | Goold | |
| 2,514,575 A | 7/1950 | Hein | |
| 2,616,422 A | 11/1952 | Jones | |
| 2,672,866 A | 3/1954 | Kater | |
| 2,690,179 A | 9/1954 | Fox | |
| 2,915,986 A | 12/1959 | Sisson | |
| 3,101,712 A | 8/1963 | Strazdins et al. | |
| 3,166,070 A | 1/1965 | Everett | |
| 3,199,511 A | 8/1965 | Kulick | |
| 3,412,906 A | 11/1968 | Dinger | |
| 3,507,278 A | 4/1970 | Werding | |
| 3,527,215 A * | 9/1970 | De Witt | A61J 1/2096 |
| | | | 604/214 |
| 3,699,961 A | 10/1972 | Szpur | |
| 3,736,932 A * | 6/1973 | Satchell | A61M 5/178 |
| | | | 604/190 |
| 3,785,367 A | 1/1974 | Fortin et al. | |
| 3,998,223 A | 12/1976 | Dawe | |
| 4,041,944 A | 8/1977 | Rhodes | |
| 4,131,217 A * | 12/1978 | Sandegren | B65D 83/0094 |
| | | | 222/103 |
| 4,140,117 A | 2/1979 | Buckles et al. | |
| 4,236,516 A | 12/1980 | Nilson | |
| 4,245,655 A | 1/1981 | Patel | |
| 4,312,344 A | 1/1982 | Nilson | |
| 4,318,400 A | 3/1982 | Peery et al. | |
| 4,325,369 A | 4/1982 | Nilson | |
| 4,419,096 A | 12/1983 | Leeper et al. | |
| 4,438,845 A | 3/1984 | Mochow | |
| 4,444,310 A | 4/1984 | Odell | |
| 4,741,733 A | 5/1988 | Winchell et al. | |
| 4,747,839 A * | 5/1988 | Tarello | A61M 5/286 |
| | | | 128/DIG. 18 |
| 4,824,145 A * | 4/1989 | Carlsson | A61M 39/10 |
| | | | 285/331 |
| 4,904,239 A | 2/1990 | Winchell et al. | |
| 5,011,477 A | 4/1991 | Winchell et al. | |
| 5,033,631 A | 7/1991 | Nightingale | |
| 5,048,684 A | 9/1991 | Scott | |
| 5,120,315 A | 6/1992 | Hessel | |
| 5,147,311 A | 9/1992 | Pickhard | |
| 5,178,610 A | 1/1993 | Tsujikawa et al. | |
| 5,192,272 A | 3/1993 | Faure | |
| 5,199,567 A | 4/1993 | Discko, Jr. | |
| 5,237,309 A | 8/1993 | Frantz et al. | |
| 5,238,003 A | 8/1993 | Baidwan et al. | |
| 5,263,940 A | 11/1993 | Kriesel | |
| 5,312,018 A | 5/1994 | Evezich | |
| 5,316,452 A | 5/1994 | Bogen et al. | |
| 5,318,540 A | 6/1994 | Athayde et al. | |
| 5,342,313 A | 8/1994 | Campbell et al. | |
| 5,383,858 A | 1/1995 | Reilly et al. | |
| 5,399,173 A * | 3/1995 | Parks | A61J 15/0026 |
| | | | 16/2.1 |
| 5,492,147 A * | 2/1996 | Challender | F16L 29/005 |
| | | | 137/614.05 |
| 5,520,653 A | 5/1996 | Reilly et al. | |
| 5,578,005 A | 11/1996 | Sancoff et al. | |
| 5,683,369 A | 11/1997 | Tsukada | |
| 5,827,233 A | 10/1998 | Futagawa et al. | |
| 5,873,861 A | 2/1999 | Hitchins et al. | |
| 5,893,843 A | 4/1999 | Rodrigues Claro | |
| 5,899,889 A | 5/1999 | Futagawa et al. | |
| 5,957,898 A * | 9/1999 | Jepson | A61M 39/045 |
| | | | 128/912 |
| 5,976,112 A | 11/1999 | Lyza, Jr. | |
| 5,980,489 A | 11/1999 | Kriesel | |
| 6,056,724 A | 5/2000 | Lacroix | |
| 6,063,058 A | 5/2000 | Sakamoto | |
| 6,077,252 A | 6/2000 | Siegel | |
| 6,142,976 A | 11/2000 | Kubo | |
| 6,270,482 B1 | 8/2001 | Rosoff et al. | |
| 6,319,235 B1 | 11/2001 | Yoshino | |
| 6,322,542 B1 | 11/2001 | Nilson et al. | |
| 6,328,715 B1 | 12/2001 | Dragan et al. | |
| 6,450,993 B1 | 9/2002 | Lin | |
| 6,465,024 B1 | 10/2002 | Di Scala et al. | |
| 6,485,471 B1 | 11/2002 | Zivitz et al. | |
| 6,497,684 B2 | 12/2002 | Witowski | |
| 6,578,738 B1 | 6/2003 | Keller | |
| 6,620,134 B1 | 9/2003 | Trombley, III et al. | |
| 6,652,489 B2 | 11/2003 | Trocki et al. | |
| 6,723,074 B1 | 4/2004 | Halseth | |
| 6,726,657 B1 | 4/2004 | Dedig et al. | |
| 6,869,419 B2 | 3/2005 | Dragan et al. | |
| 7,011,650 B2 | 3/2006 | Rosoff et al. | |
| 7,094,216 B2 | 8/2006 | Trombley, III et al. | |
| 7,240,926 B2 * | 7/2007 | Dalle | A61M 39/1011 |
| | | | 285/307 |
| 7,419,478 B1 | 9/2008 | Reilly et al. | |
| 7,462,166 B2 | 12/2008 | Cowan et al. | |
| 7,497,843 B1 | 3/2009 | Castillo et al. | |
| 7,540,856 B2 | 6/2009 | Hitchins et al. | |
| 7,556,619 B2 | 7/2009 | Spohn et al. | |
| 7,581,559 B2 | 9/2009 | Bausmith, III et al. | |
| 7,597,683 B2 | 10/2009 | Myhrberg et al. | |
| 7,621,395 B2 | 11/2009 | Mogensen et al. | |
| 7,686,788 B2 | 3/2010 | Freyman et al. | |
| 8,147,464 B2 | 4/2012 | Spohn et al. | |
| 8,337,456 B2 | 12/2012 | Schriver et al. | |
| 2001/0018575 A1 | 8/2001 | Lyza, Jr. | |
| 2002/0147429 A1 | 10/2002 | Cowan et al. | |
| 2003/0216695 A1 | 11/2003 | Yang | |
| 2004/0064041 A1 | 4/2004 | Lazzaro et al. | |
| 2004/0068224 A1 | 4/2004 | Couvillon, Jr. et al. | |
| 2005/0113754 A1 | 5/2005 | Cowan | |
| 2006/0200083 A1 | 9/2006 | Freyman | |
| 2007/0129705 A1 * | 6/2007 | Trombley, III | A61M 39/10 |
| | | | 604/523 |
| 2008/0086087 A1 | 4/2008 | Spohn et al. | |
| 2009/0069792 A1 * | 3/2009 | Frey | A61M 25/0009 |
| | | | 604/535 |
| 2009/0216192 A1 | 8/2009 | Schriver et al. | |
| 2009/0218243 A1 | 9/2009 | Gyrn et al. | |
| 2010/0089475 A1 | 4/2010 | Tracey | |
| 2012/0123257 A1 | 5/2012 | Stokes, Jr. et al. | |
| 2012/0209111 A1 | 8/2012 | Cowan et al. | |

FOREIGN PATENT DOCUMENTS

| | | |
|---|---|---|
| WO | 2004033023 A1 | 4/2004 |
| WO | 2013043868 A1 | 3/2013 |
| WO | 2013043881 A1 | 3/2013 |
| WO | 2013043889 A1 | 3/2013 |

OTHER PUBLICATIONS

The International Preliminary Report on Patentability and Written Opinion mailed on Sep. 24, 2015 from corresponding PCT Application No. PCT/US2014/022629.

(56) References Cited

OTHER PUBLICATIONS

"Supplementary European Search Report from EP 14770001", Nov. 25, 2016.

* cited by examiner

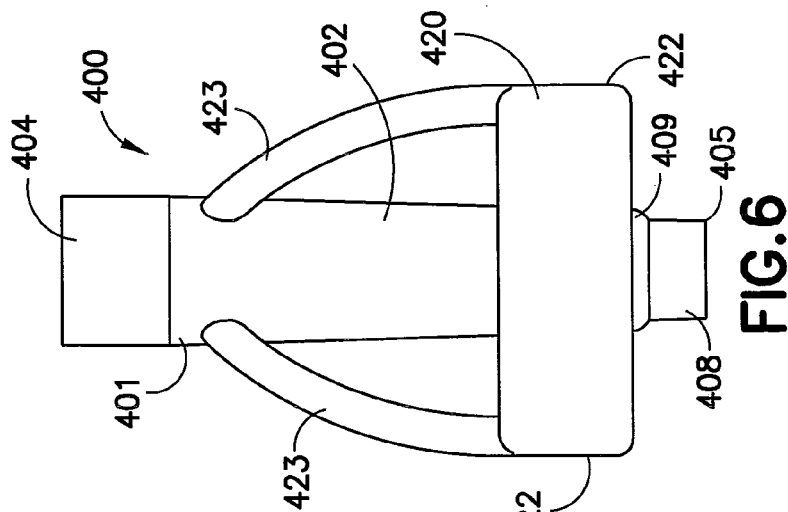
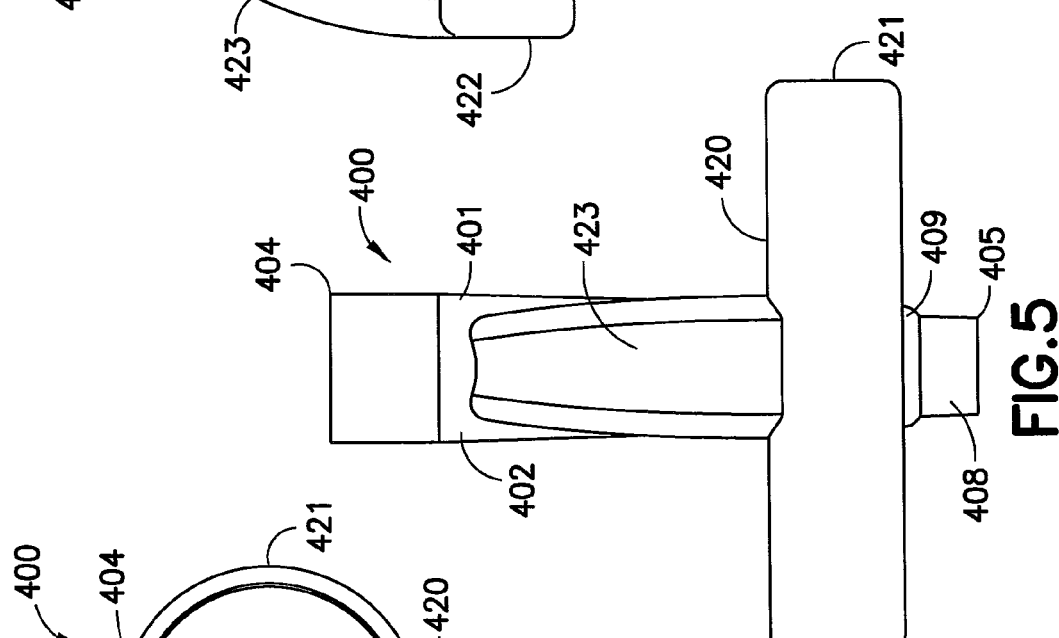
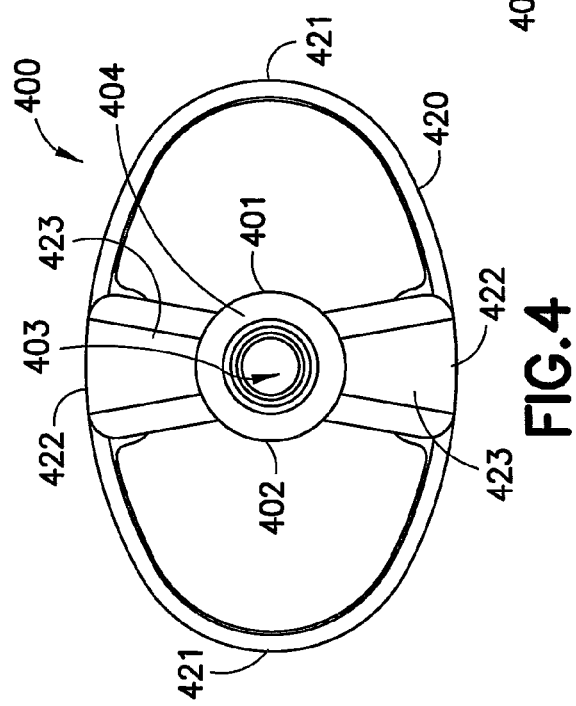

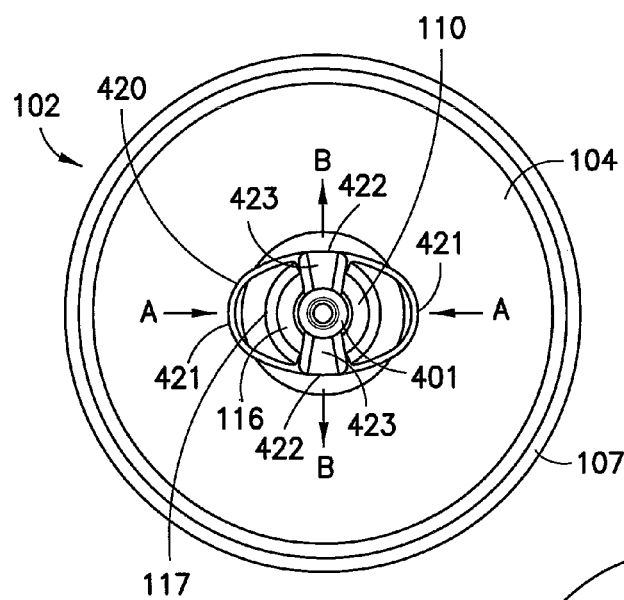
FIG.14
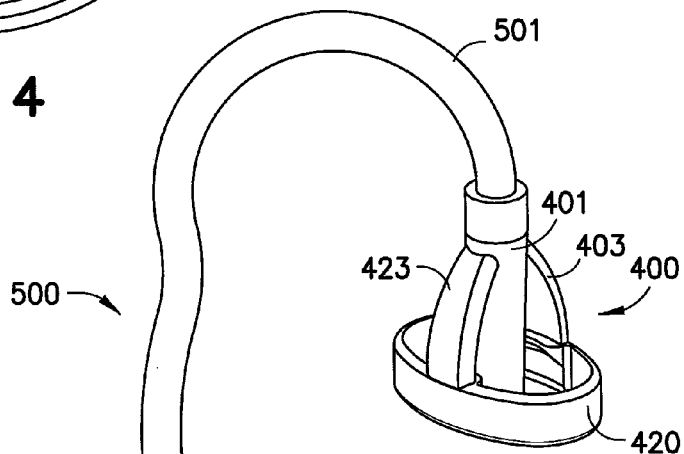
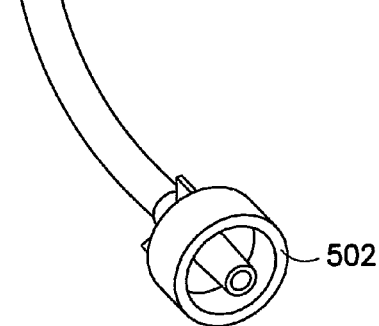
FIG.15

CONNECTOR ASSEMBLY FOR SYRINGE SYSTEM

BACKGROUND OF THE INVENTION

Field of the Invention

The present disclosure is related to the medical field and, more particularly, to disposable syringes and connectors therefore used in the medical field in which all or part of the syringe and/or connector may be disposed of after a single use.

Description of Related Art

It is well known that syringes used in the medical field are typically disposable and are discarded after one use. These syringes usually comprise a barrel and a plunger mounted for reciprocal movement in the barrel, both parts usually being made of plastic material. Although disposable syringes are typically made by mass production methods, such as injection molding, such disposable syringes are relatively expensive due to the materials and precision involved in their manufacture.

Such disposable syringes typically include one or more fluid outlets and inlets that place the interior of the barrel of the syringe in fluid communication with one or more sources of treatment or testing fluids, with the patient for administering the fluids, and with one or more fluid waste containers. The inlets/outlets may be integrally formed with the barrel of the syringe and caps may be removably attached to the inlets/outlets for sterility. Typically, the caps and inlets/outlets are formed with a standard threaded luer or similar configuration to allow for connection of the inlet/outlet to a tubing element of a fluid set. However, such standard luer engagements require a technician or user to spend a good deal of time assembling the tubing elements, which may be long and unwieldy, to the inlets/outlets of the syringes, and possibly an even greater amount of time disassembling these engagements. This leads to greater preparation and turn-around times for every use of a fluid delivery system, and, thus, fewer overall uses of the fluid delivery system and its facilities. Further, manufacturing plastic components with threaded luer engagements leads to greater material costs since the cap or syringe must be molded with the threaded luer adapter integrally formed thereon. The cap and/or syringe are typically disposed of after a single use, leading to a higher cost per patient for use of the fluid delivery system.

SUMMARY OF THE INVENTION

Accordingly, there is a general need in the art for a connector that quickly and effectively connects and disconnects a tubing element to and from a discharge outlet of a cap and/or barrel of a syringe of a fluid delivery system and that is able to withstand the fluid pressures generated during use of the fluid delivery system. Further, use of such a connector should reduce the overall manufacturing costs of the disposable components of the syringe.

According to an embodiment of this disclosure, a cap-bladder and luer assembly for a fluid delivery system is provided. The assembly includes a cap including a cap body having an internal surface defining an interior cavity and a discharge outlet disposed on an exterior of the cap body; a disc-shaped bladder disposed within the interior cavity of the cap body and operatively connected to the internal surface of the cap body, the disc-shaped bladder including a membrane portion; and a snap luer connector removably attached to the discharge outlet of the cap. The discharge outlet includes a sidewall extending between a distal end and a proximal end connected to the exterior of the cap body, the sidewall defining an internal passage in fluid communication with the interior cavity by way of a discharge orifice extending through the cap body. The snap luer connector includes a central body having a sidewall and configured to be at least partially positioned within the internal passage of the discharge outlet, and a connector portion connected to the central body and configured to releasably engage the sidewall of the discharge outlet, the sidewall of the central body defining an internal channel within the central body that is in fluid communication with the interior cavity of the cap body when the snap luer connector is attached to the discharge outlet.

The sidewall of the central body of the snap luer connector may extend from a distal end of the central body to a proximal end of the central body and define a distal portion that extends beyond the distal end of the discharge outlet, and a proximal portion that is positioned within the internal passage of the discharge outlet when the snap luer connector is attached to the discharge outlet. The internal channel of the central body may extend from the distal end of the central body to the proximal end of the central body. The sidewall of the proximal portion of the central body of the snap luer connector may be contoured to correspond to a shape of the internal passage of the discharge outlet. The central body of the snap luer connector may include a narrowed tip defined at the proximal end of the central body, the narrowed tip being configured to extend into the discharge orifice of the cap and terminate flush with the interior surface of the cap. A portion of the internal channel in the distal portion of the central body of the snap luer connector may define a female luer fitting configured to releasably engage a tubing element.

In a further embodiment, the connector portion of the snap luer connector includes an elliptical connector ring connected to the central body and surrounding the proximal portion of the central body. The elliptical connector ring has two opposing major vertices and two opposing minor vertices. The elliptical connector ring is connected to the distal portion of the central body by at least two radially and proximally extending arms, each extending between the distal portion of the central body and one of the minor vertices of the elliptical connector ring. The sidewall of the discharge outlet includes a conical tip defined at the distal end of the discharge outlet, the conical tip defining a flange having a proximally facing abutment surface that surrounds the sidewall of the discharge outlet. The elliptical connector ring of the snap luer connector includes at least two inward radially-extending flanges positioned at the minor vertices of the elliptical connector ring, the inward radially-extending flanges defining distally facing abutment surfaces that engage the abutment surface of the flange of the conical tip of the discharge outlet when the snap luer connector is attached to the discharge outlet. The abutment surfaces of the conical tip of the discharge outlet and the inward radially-extending flanges of the elliptical connector ring are configured to be disengaged by pressing the major vertices of the elliptical connector ring towards each other.

In another embodiment of this disclosure, a bladder syringe and luer connector for a fluid delivery system is provided. The bladder syringe and luer connector include a cylindrical body having a distal end and a proximal end and defining a throughbore and a cap-bladder assembly adapted for connection to the distal end of the cylindrical body. The cap-bladder assembly includes a cap including a cap body having an internal surface defining an interior cavity and a discharge outlet disposed on an exterior of the cap body, and a disc-shaped bladder disposed within the interior cavity of the cap body and operatively connected to the internal surface of the cap body, the disc-shaped bladder including a membrane portion. The bladder syringe and luer connector also include a plunger element disposed in the throughbore of the cylindrical body and a snap luer connector removably attached to the discharge outlet of the cap. A portion of the plunger element and the membrane portion of the bladder are interactively shaped. The discharge outlet of the cap includes a sidewall extending between a distal end and a proximal end connected to the exterior of the cap body, the sidewall defining an internal passage in fluid communication with the interior cavity by way of a discharge orifice extending through the cap body. The snap luer connector includes a central body having a sidewall and configured to be at least partially positioned within the internal passage of the discharge outlet and a connector portion connected to the central body and configured to releasably engage the sidewall of the discharge outlet, the sidewall of the central body defining an internal channel within the central body that is in fluid communication with the interior cavity of the cap body when the snap luer connector is attached to the discharge outlet.

According to yet another embodiment of this disclosure, a method of releasably connecting a tubing element to a bladder syringe for a fluid delivery system is provided. The method includes the step of providing the bladder syringe. The bladder syringe includes a cylindrical body having a distal end and a proximal end and defining a throughbore and a cap-bladder assembly adapted for connection to the distal end of the cylindrical body. The cap-bladder assembly includes a cap including a cap body having an internal surface defining an interior cavity and a discharge outlet disposed on an exterior of the cap body, and a disc-shaped bladder disposed within the interior cavity of the cap body and operatively connected to the internal surface of the cap body, the disc-shaped bladder including a membrane portion. The bladder syringe also includes a plunger element disposed in the throughbore of the cylindrical body. The discharge outlet of the cap includes a sidewall extending between a distal end and a proximal end connected to the exterior of the cap body, the sidewall defusing an internal passage in fluid communication with the interior cavity by way of a discharge orifice extending through the cap body, and the discharge outlet further includes a conical tip defined at the distal end of the discharge outlet, the conical tip defining a flange having a proximally facing abutment surface that surrounds the sidewall of the discharge outlet. The method also includes the step of providing a snap connector including a central body having a sidewall and an elliptical connector ring connected to and surrounding the central body, the sidewall of the central body defining an internal channel within the central body. The elliptical connector ring has two opposing major vertices and two opposing minor vertices, and at least two inward radially-extending flanges positioned at the minor vertices of the elliptical connector ring, the inward radially-extending flanges defining distally facing abutment surfaces. The method further includes the steps of inserting the tubing element into a portion of the internal channel of the central body of the snap connector to releasably connect the tubing element to the central body; positioning a portion of the central body of the snap connector within the internal passage of the discharge outlet such that the internal channel of the central body of the snap connector is in fluid communication with the interior cavity of the cap body; and engaging the abutment surface of the flange of the conical tip of the discharge outlet with the abutment surfaces of the inward radially-extending flanges of the elliptical connector ring to connect the snap connector to the discharge outlet of the cap.

The method may further include the step of pressing inward on the elliptical retaining ring at the major vertices to disengage the abutment surfaces of the inward radially-extending flanges from the abutment surface of the flange of the conical tip of the discharge outlet and disconnect the snap connector from the discharge outlet.

According to a further embodiment, a connector assembly for a fluid delivery system is provided. The connector assembly includes a conical body defining an interior cavity and a discharge outlet, the discharge outlet defining an internal passage in fluid communication with the interior cavity; and a connector removably attached to the discharge outlet, the connector including a central body configured to be at least partially positioned within the internal passage of the discharge outlet, and including an annular connector portion connected to the central body and configured to releasably engage an exterior of the discharge outlet, the central body defining an internal channel within the central body that is in fluid communication with the interior cavity of the conical body when the connector is attached to the discharge outlet.

The central body of the connector may define a distal portion that extends beyond a distal end of the discharge outlet and a proximal portion that is positioned within the internal passage of the discharge outlet when the connector is attached to the discharge outlet. A proximal portion of the central body of the connector may be contoured to correspond to a shape of the internal passage of the discharge outlet. The central body may include a narrowed tip defined at a proximal end of the central body, the narrowed tip being configured to extend into the internal passage and terminate substantially flush with an interior surface of the conical body. A portion of the internal channel in the central body may define a luer fitting configured to releasably engage a tubing element. The annular connector portion may include a ring connected to the central body and surrounding the central body. The ring may be elliptical and have two opposing major vertices and two opposing minor vertices. The ring may be connected to the distal portion of the central body by at least two radially and proximally extending arms each extending between the distal portion of the central body and one of the minor vertices of the ring. The sidewall of the discharge outlet may include a conical tip defined at the distal end of the discharge outlet, the conical tip defining a flange having a proximally facing abutment surface that surrounds the sidewall of the discharge outlet. The elliptical connector ring of the snap connector may include at least two inward radially-extending flanges positioned at the minor vertices of the elliptical connector ring, the inward radially-extending flanges defining distally facing abutment surfaces that engage the abutment surface of the flange of the conical tip of the discharge outlet when the snap connector is attached to the discharge outlet. The abutment surfaces of the conical tip of the discharge outlet and the inward radially-extending flanges of the elliptical connector ring may be configured to be disengaged by pressing the major vertices of the elliptical connector ring towards each other.

According to a further embodiment, a cap-bladder and connector assembly for a fluid delivery system is provided. The cap-bladder and connector assembly includes a cap body defining an interior cavity and a discharge outlet, the discharge outlet defining an internal passage in fluid communication with the interior cavity; a disc-shaped bladder disposed within the interior cavity of the cap body and connected to an internal surface of the cap body; and a connector removably attached to the discharge outlet, the connector including a central body configured to be at least partially positioned within the internal passage of the discharge outlet, and including an annular connector portion connected to the central body and configured to releasably engage the discharge outlet, the central body defining an internal channel within the central body that is in fluid communication with the interior cavity of the conical body when the connector is attached to the discharge outlet.

The central body of the connector may define a distal portion that extends beyond a distal end of the discharge outlet and a proximal portion that is positioned within the internal passage of the discharge outlet when the connector is attached to the discharge outlet. The proximal portion of the central body of the connector may be contoured to correspond to a shape of the internal passage of the discharge outlet. The central body may include a narrowed tip defined at a proximal end of the central body, the narrowed tip being configured to extend into the internal passage and terminate substantially flush with an interior surface of the conical body. The annular connector portion may include a ring connected to the central body and surrounding the central body. The ring may be elliptical and have two opposing major vertices and two opposing minor vertices. The ring may be connected to the distal portion of the central body by at least two radially and proximally extending arms each extending between the distal portion of the central body and one of the minor vertices of the ring.

According to another embodiment, a connector assembly is provided. The connector assembly includes a first connector element including a sidewall extending between a proximal end and a distal end and defining an internal passage therebetween; and a second connector element removably attached to the first connector element, the second connector element including a central body configured to be at least partially positioned within the internal passage of the first connector element, and including an annular connector portion connected to the central body, the annular connector portion being configured to releasably engage an exterior of the sidewall of the first connector element when the second connector element is attached to the first connector element, the central body defining an internal channel within the central body that is in fluid communication with the internal passage of the first connector element when the second connector element is attached to the first connector element.

The central body of the second connector element may define a distal portion that extends beyond the distal end of the first connector element and a proximal portion that is positioned within the internal passage when the second connector element is attached to the first connector element. A proximal portion of the central body of the second connector element may be contoured to correspond to a shape of the internal passage of the first connector element. The central body may include a narrowed tip defined at a proximal end of the central body, the narrowed tip being configured to extend into the internal passage and terminate substantially flush with the proximal end of the first connector element. The annular connector portion may include a ring surrounding the central body and the ring may be elliptical and have two opposing major vertices and two opposing minor vertices. The ring may be connected to the distal portion of the central body by at least two radially and proximally extending arms each extending between the distal portion of the central body and one of the minor vertices of the ring. The sidewall of the first connector element may define a distal end flange having a proximally-facing abutment surface, and the ring of the second connector element may include at least two inward radially-extending flanges positioned at the minor vertices of the ring, the inward radially-extending flanges defining distally facing abutment surfaces that engage the abutment surface of the distal flange when the second connector element is connected to the first connector element. The abutment surfaces of the inward radially-extending flanges of the ring may be configured to be disengaged from the proximally-facing abutment surface of the distal end flange by pressing the major vertices of the ring towards each other. The sidewall of the first connector element may define at least one additional flange having a proximally-facing abutment surface, the at least one additional flange being defined proximally of the distal end flange.

According to another embodiment, a method of releasably establishing a fluid path for a fluid delivery system using a connector assembly is provided. The method includes the steps of providing a conical body having an internal surface defining an interior cavity and a discharge outlet extending distally from the conical body and defining a discharge orifice, the discharge outlet including a sidewall defining an internal passage in fluid communication with the interior cavity; and removably connecting a snap connector to the discharge outlet, the snap connector including a central body having a sidewall and configured to be at least partially positioned within the internal passage of the discharge outlet, and including a connector portion connected to the central body and configured to releasably engage the sidewall of the discharge outlet, the sidewall of the central body defining an internal channel within the central body that is in fluid communication with the interior cavity of the conical body when the snap connector is attached to the discharge outlet.

The connector portion may include a connector ring connected to and surrounding the central body, the connector ring including at least two inward radially-extending flanges defining distally facing abutment surfaces, the discharge outlet including a mating flange defining a mating abutment surface and the method may further include positioning a portion of the central body of the snap connector within the internal passage of the discharge outlet such that the internal channel of the central body of the snap connector is in fluid communication with the interior cavity of the cap body; and engaging the mating abutment surface of the mating flange of the discharge outlet with the abutment surfaces of the inward radially-extending flanges of the connector ring to connect the snap connector to the discharge outlet of the cap. The connector ring may be elliptical and have two opposing major vertices and two opposing minor vertices, and the method may further include pressing inward on the elliptical connector ring at the major vertices to disengage the abutment surfaces of the inward radially-extending flanges from the mating abutment surface of the mating flange of the discharge outlet to disconnect the snap connector from the discharge outlet.

According to another embodiment, a fluid delivery system is provided. The fluid delivery system includes a fluid pump device defining an interior cavity and a discharge outlet, the discharge outlet defining an internal passage in fluid communication with the interior cavity; and a connector removably attached to the discharge outlet, the connector including a central body configured to be at least partially positioned within the internal passage of the discharge outlet, and including an annular connector portion connected to the central body and configured to releasably engage an exterior of the discharge outlet, the central body defining an internal channel within the central body that is in fluid communication with the interior cavity of the conical body when the connector is attached to the discharge outlet.

Further details and advantages will be understood upon reading the following detailed description in conjunction with the accompanying drawings, wherein like parts are designated with like reference numerals throughout the several views.

BRIEF DESCRIPTION OF THE DRAWINGS

FIG. 4 is a top view of a snap connector for use with the bladder syringe and fluid delivery system of FIG. 1 in accordance with an embodiment of this disclosure;

FIG. 5 is a front view of the snap connector of FIG. 4;

FIG. 6 is a side view of the snap connector of FIG. 4;

FIG. 14 is a top view of the cap and the snap connector of FIG. 9 when attached;

FIG. 15 is an upper perspective view of the snap connector of FIG. 4 and a tubing element in accordance with an embodiment of this disclosure.

DESCRIPTION OF THE PREFERRED EMBODIMENTS

For purposes of the description hereinafter, spatial orientation terms, as used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific components, devices, and features illustrated in the accompanying drawing figures and described herein are simply exemplary and should not be considered as limiting.

Figure 1:
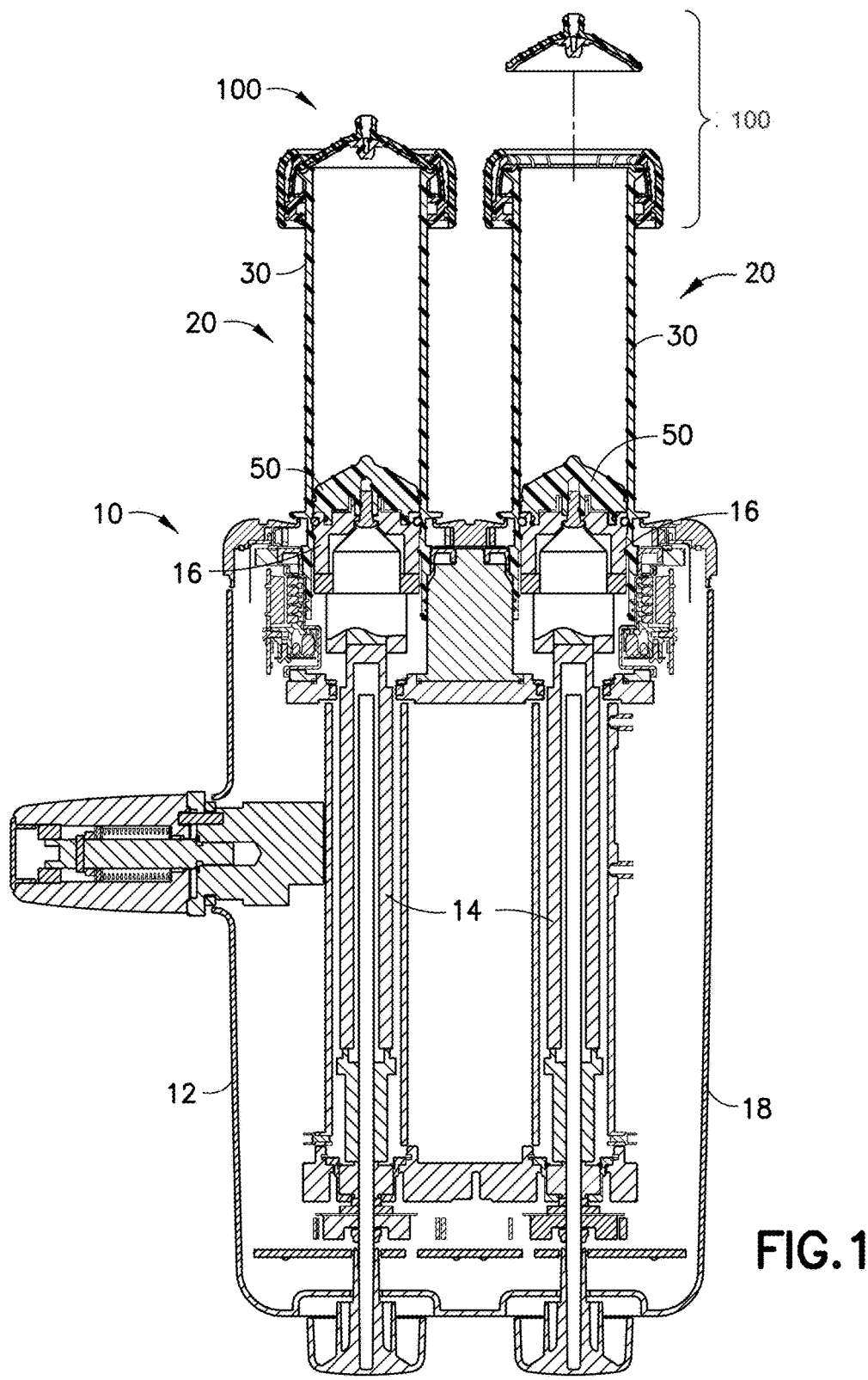
FIG. 1 is a cross-sectional side view of a fluid delivery system utilizing a bladder syringe in accordance with one embodiment of this disclosure.

With reference to FIG. 1, a fluid delivery system 10 is shown in accordance with an embodiment of this disclosure. The fluid delivery system 10 generally includes a power fluid injector head 12, such as a Stellant® power injector platform manufactured by Medrad, Inc., and a bladder syringe 20 as described in detail herein. As is known in the medical field, injecting contrast media into the bloodstream of patients enables visualization of various pathologies through X-Ray, Computed Tomography (CT), Magnetic Resonance (MR), or other medical imaging modalities. Contrast delivery is most effective and efficient using a power injector, such as the Stellant® power injector, that can be programmed to deliver specific amounts of contrast agent and/or saline at specific flow rates. A power injector may be used in diagnosing stroke, heart disease, cancer, vascular disease, physical injury, digestive disorder, etc. The fluid injector 12 comprises two (2) linearly reciprocal piston elements 14, which each have a distal piston interface 16 adapted to engage a syringe plunger disposed within a syringe body. The piston elements 14 are enclosed within a housing 18 and specific details of a power injector platform and syringe elements used therewith may be found in U.S. Pat. No. 5,383,858 to Reilly et al.; U.S. Pat. No. 5,873,861 to Hitchins et al.; and U.S. Pat. No. 6,652,489 to Trocki et al., all assigned to Medrad, Inc. and each incorporated herein by reference for disclosure related to the foregoing elements. This disclosure is explicitly not limited to utilizing the bladder syringe 20 with contrast media but may be used for any medicinal or diagnostic fluid to be delivered to a patient.

Figure 2:
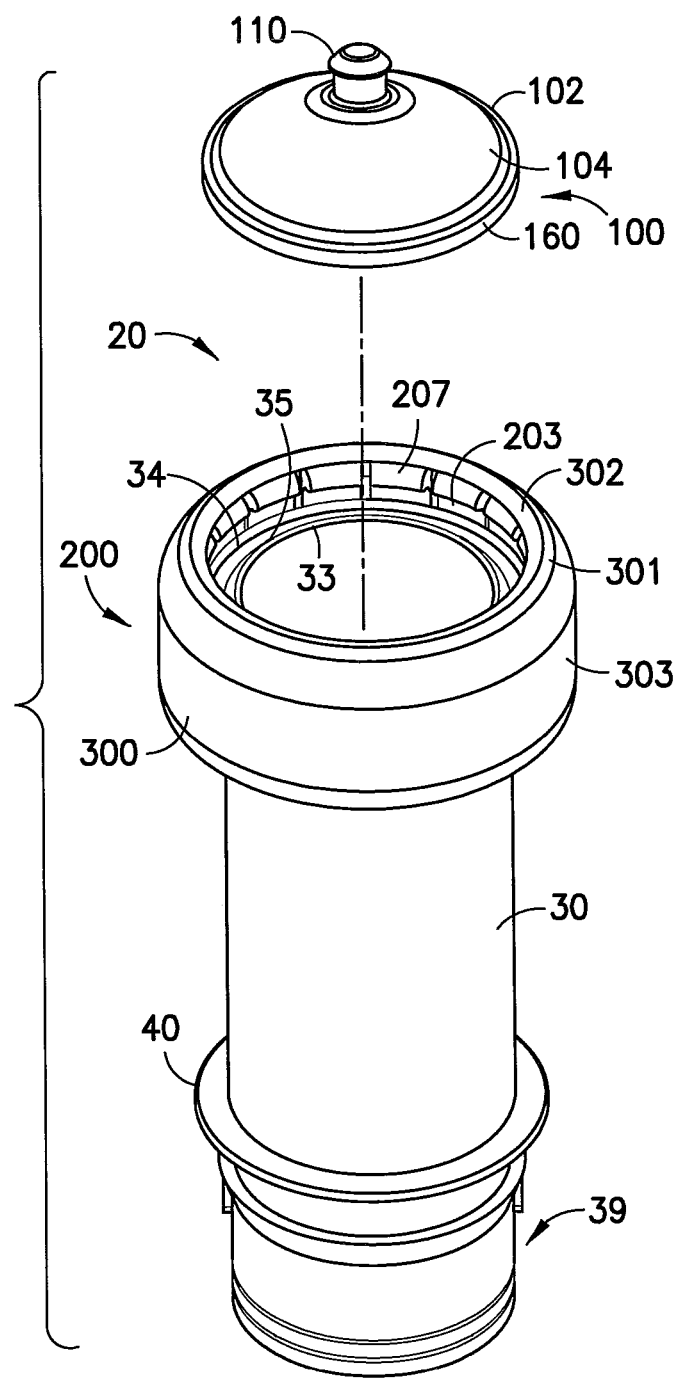
FIG. 2 is a partially exploded perspective view of the bladder syringe shown in FIG. 1.
Figure 3:
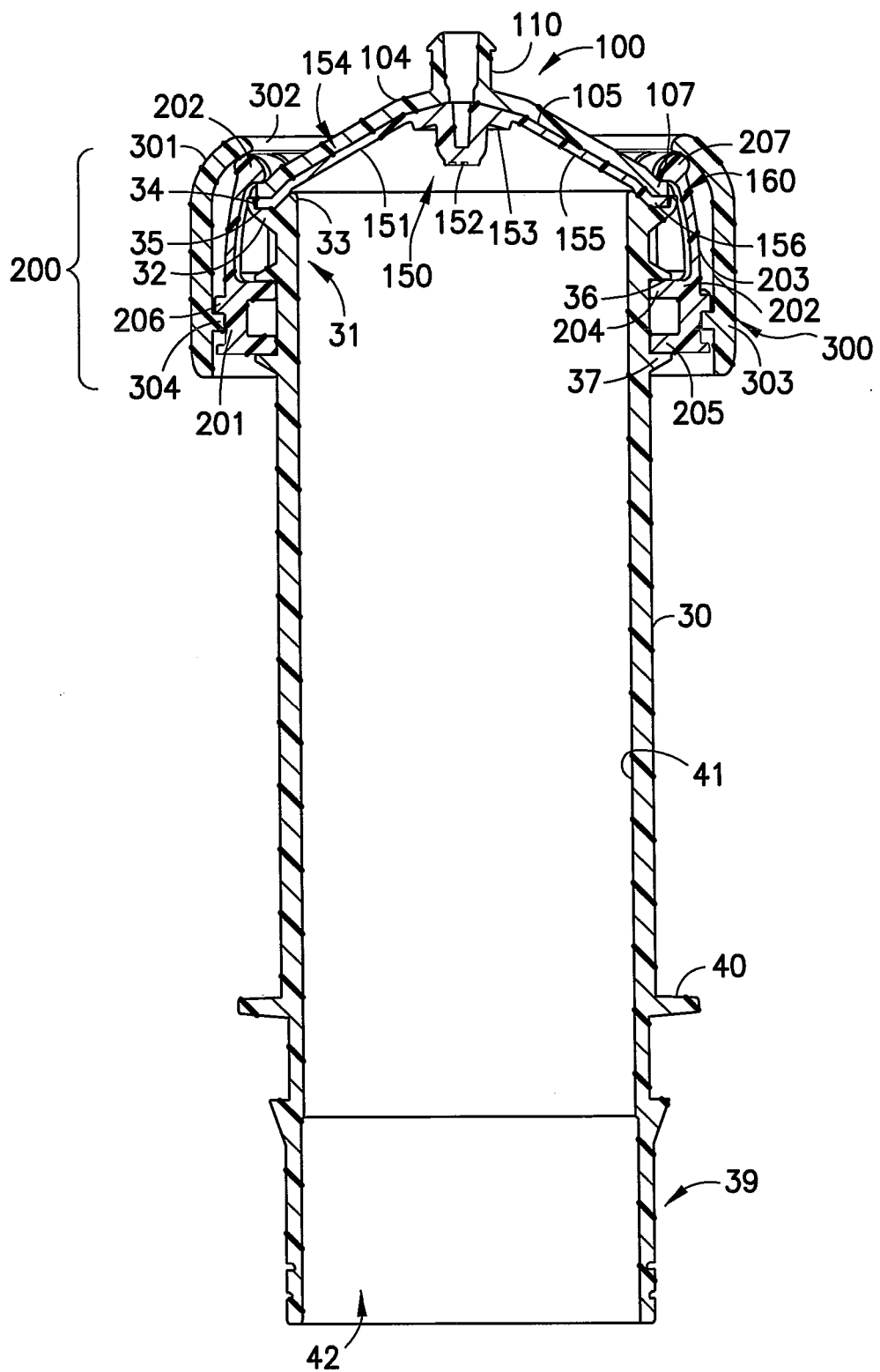
FIG. 3 is a longitudinal cross-sectional side view of the bladder syringe shown in FIG. 1.
Figure 7:
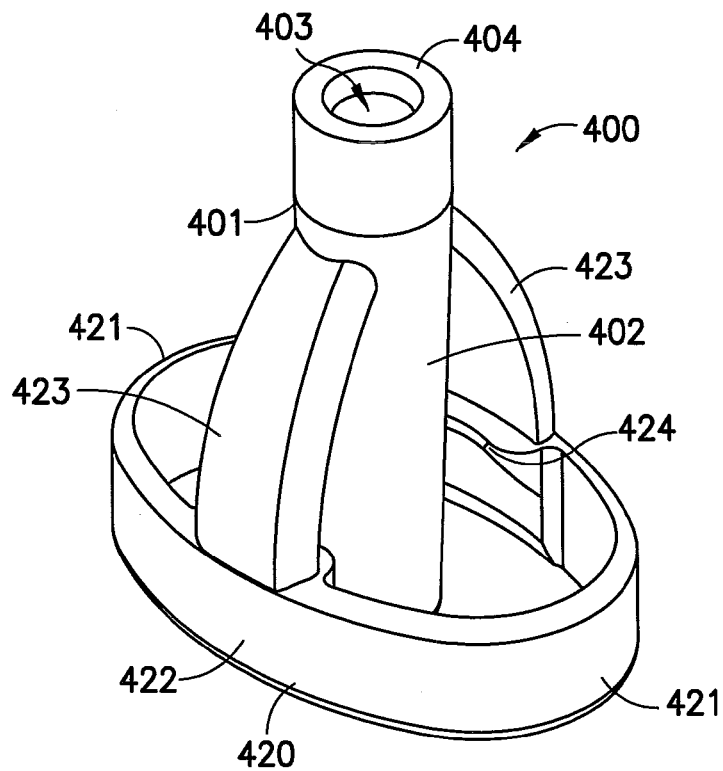
FIG. 7 is an upper perspective view of the snap connector of FIG. 4.
Figure 8:
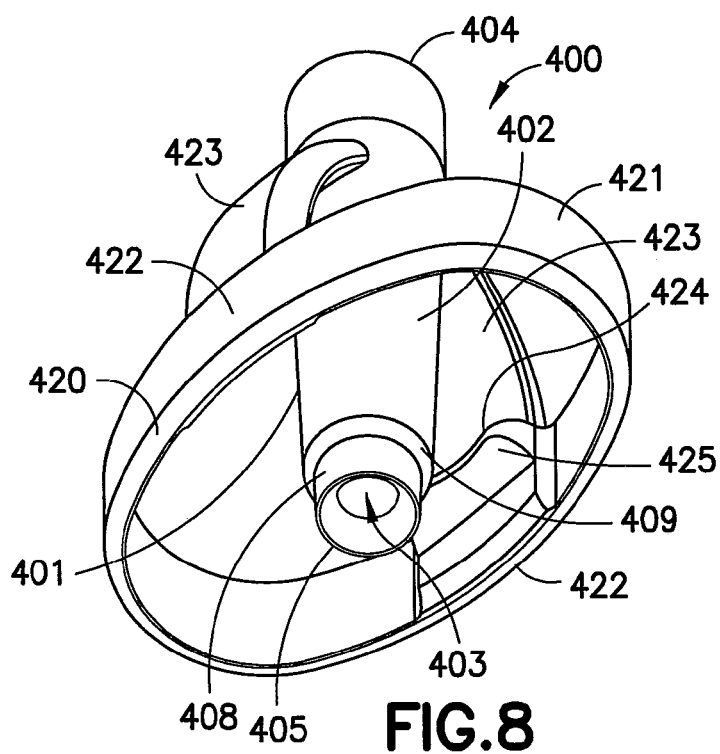
FIG. 8 is a lower perspective view of the snap connector of FIG. 4.
Figure 9:
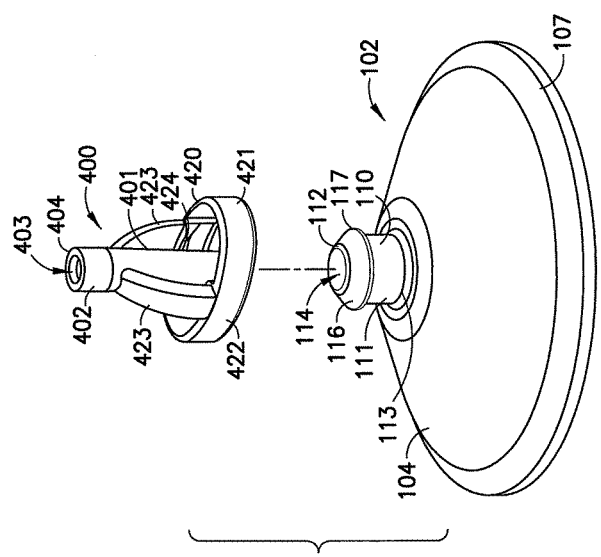
FIG. 9 is an exploded perspective view of a cap of the bladder syringe of FIG. 1 and the snap connector of FIG. 4 in accordance with an embodiment of this disclosure.

The bladder syringe 20 is a multi-component or composite device of the type illustrated in and discussed, for example, with reference to FIGS. 73A-73E of co-pending U.S. application Ser. No. 13/453,335, assigned to Medrad, Inc. and incorporated herein by reference in its entirety. In particular, as shown in FIGS. 1-3, the bladder syringe 20 includes a cylindrical body 30, a plunger element 50 disposed in the cylindrical body 30, a cap-bladder assembly 100, a flex-leg connecting assembly 200, and a rotating outer sleeve 300. The cap-bladder assembly 100 may be of a type similar to any one of the embodiments disclosed in U.S. application Ser. No. 13/453,335, as referred to above. And, in particular, may be substantially similar to the embodiment illustrated in and discussed with reference to FIG. 47C of U.S. application Ser. No. 13/453,335.

As shown in FIGS. 2, 3, and 11-13, the cap-bladder assembly 100 includes cap 102 having a cap body 104, which may be formed with a conical shape to define a conical cap body 104. The cap body 104 has an internal surface 105, which defines an interior cavity 106, and a discharge outlet 110 disposed on an exterior of the cap body 104. A disc-shaped bladder 150 is disposed within the interior cavity 106 of the cap body 104 and is operatively connected to the inner perimeter of the internal surface 105 of the cap body 104. The disc-shaped bladder 150, which may be co-injection molded with the cap body 104, includes a membrane portion 151 having a central well portion 152. The central well portion 152 is surrounded by a thickened circumferential region 153. The membrane portion 151 generally conforms to the internal shape of the interior cavity 106 of the cap body 104, and includes a distal side 154 an opposing proximal side 155. The membrane portion 151 includes a central well portion 152 and a surrounding thickened circumferential region 153, and defines a profile or shape that interacts with the profile of the plunger element 50. Additionally, the bladder 150 and the cap body 104 have outer circumferential rims or flanges 156, 107, respectively, that may be joined together in the co-injection molding process. As an alternative, the outer circumferential flanges or rims 107, 156 may be joined by other joining methods, such as ultrasonic welding, laser welding, adhesive joining, and like joining techniques. Accordingly, as shown in FIG. 3, an exterior circumferential rim 107 of the cap body 104 is joined to an exterior circumferential rim 156 of the bladder 150 and a composite end flange or rim 160 is defined by this molded joint. The bladder syringe 20 is adapted for use in CT, MR, and like procedures, and operable at typical operating pressures of about 300-400 psi, and the bladder 150 may be expanded to hold fluid volumes on the order of 200 ml.

The cylindrical body 30 is a unitary, typically, cylindrical body having a distal end 31 and a proximal end 39 and is typically a reusable component, while the cap-bladder assembly 100 is typically a single-use component. The cylindrical body 30 has an interior wall 41 that defines a throughbore 42 between the distal and proximal ends 31, 39. The distal end 31 of the cylindrical body 30 includes an enlarged end flange or rim 32 with inner and outer circumferential walls 33, 34 that define an annular recess 35 therebetween. The inner circumferential wall 33 is slightly larger in height and tapered as compared to the outer circumferential wall 34. The composite end flange 160 of the cap-bladder assembly 100 is configured to be received within the annular recess 35. Additionally, two (2) axially-spaced radial flanges 36, 37 are provided on the cylindrical body 30 axially below the end flange or rim 32. A pair of axial walls (not shown) extend between the radial flanges 36, 37, which act as rotation stops as described herein. The proximal end 39 of the cylindrical body 30 is formed with a circumferential flange 40 positioned to engage the front end of the housing 18 of the fluid injector head 12 to properly seat the cylindrical body 30 relative to the fluid injector head 12. A suitable connecting arrangement for mounting the proximal end 39 of the cylindrical body 30 to a power fluid injector may be found in U.S. Pat. No. 7,540,856 to Hitchins et al., which is incorporated herein by reference in its entirety.

The plunger element 50 may be of any of the types described with reference to the various embodiments disclosed in U.S. application Ser. No. 13/453,335. The operation of the plunger element 50 by the power fluid injector head 12 and its interaction with the cylindrical body 30 and the disc-shaped bladder 150 of the cap-bladder assembly 100 is described in detail with reference to the various embodiments disclosed in U.S. application Ser. No. 13/453,335.

The cap-bladder assembly 100 is connected to the distal end 31 of the cylindrical body 30 by the flex-leg connecting assembly 200 and the rotating outer sleeve 300. The flex-leg connecting assembly 200 includes a composite flex legs inner sleeve 201 disposed within the rotating outer sleeve 300. The composite flex legs inner sleeve 201 is a split-ring component formed by two (2) opposing split-ring halves 202, which each have a plurality of distally-extending contact flex legs 203. The interior of each of the split-ring halves 202 has a pair of radially inward extending flanges 204, 205 adapted to be received and sandwiched between the two (2) radially outward extending flanges 36, 37 on the cylindrical body 30. The exterior of each of the split-ring halves 202 includes a series of external threads 206. The opposing free ends of the split-ring halves 202 may be adapted for frictional engagement, if desired, to secure the two (2) split-ring halves 202 together, or a locking connection (not shown) may be provided to secure the free ends. The pair of axial walls that extend between the radial flanges 36, 37 on the cylindrical body 30 may engage a recess or groove (not shown) in the interior of the opposing split-ring halves 202 and this engagement acts as rotation stops to prevent rotation of the composite flex legs inner sleeve 201 once assembled by joining the two (2) split-ring halves 202 together around the cylindrical body 30.

The outer sleeve 300 includes a curved distal end or portion 301 that defines an opening 302 sized to receive the cap-bladder assembly 100 therethrough, and is adapted to fit over the composite flex legs inner sleeve 201. The outer sleeve 300 has a sidewall 303 extending from the distal end or portion 301 that is of a sufficient axial length to entirely enclose the composite flex legs inner sleeve 201. The interior side of the sidewall 303 includes mating threads 304 to engage the external threads 206 on the exterior of each of the split-ring halves 202. The outer sleeve 300 is connected to the composite flex legs inner sleeve 201 by threaded engagement between the mating threads 206, 304. When the outer sleeve 300 is rotated relative to the inner sleeve 201, the outer sleeve 300 is either drawn axially downward along the inner sleeve 201 or moves axially upward along the inner sleeve 201. In an open position of the flex-leg connecting assembly 200, the outer sleeve 300 is in a position relative to the inner sleeve 201 to radially position the contact flex legs 203 at a radial position that allows the cap-bladder assembly 100 to be inserted through the distal opening 302 and be connected to the cylindrical body 30. In this connection or engagement, the composite end flange or rim 160 defined by the exterior circumferential rim 107 of the cap body 104 and the exterior circumferential rim 156 of the bladder 150 is received in the annular recess 35 defined between the inner and outer circumferential walls 33, 34 of the enlarged end flange or rim 32 on the distal end 31 of the cylindrical body 30. To secure this engagement, the outer sleeve 300 is rotated, for example clockwise, relative to the inner sleeve 201 to arrive at the closed position, shown in FIG. 3, wherein the flex legs 203 are displaced radially inward to engage the composite end flange or rim 160 which secures the cap-bladder assembly 100 in place. As shown in FIG. 3, the clockwise rotational movement of the outer sleeve 300 causes the mating threads 206, 304 to draw the outer sleeve 300 axially downward along the inner sleeve 201, and this motion causes the internally curved distal end or portion 301 of the outer sleeve 300 to contact an externally curved distal end 207 on each of the flex legs 203 and deflects the flex legs 203 radially inward to engage the composite end flange or rim 160 on the cap-bladder assembly 100. Reverse rotational movement of the outer sleeve 300 causes reverse movement and releases the flex legs 203 from the locking position shown in FIG. 3 as the outer sleeve 300 moves axially upward along the inner sleeve 201. Once the flex legs 203 disengage from the composite end flange or rim 160 on the cap-bladder assembly 100, the cap-bladder assembly 100 may be removed for disposal. The flex legs 203 are resiliently flexible to move to a release position when not acted upon by the internally curved distal end 301 of the outer ring 300. The flex-leg connecting assembly 200 has numerous advantages. For example, the loading of the cap-bladder assembly 100 is non-orientation specific and does not require rotation during assembly so that the bladder 150 is not subject to torque or twisting motion. Additionally, all components of the flex-leg connecting assembly 200 may be permanently connected to the cylindrical body 30 during manufacturing and there will be no loose parts for the end user to assemble.

With reference to FIGS. 4-15, a snap connector 400 is shown in accordance with an embodiment of this disclosure. With reference to FIGS. 9-14, the snap connector 400 is removably attachable to the discharge outlet 110 of the cap 102. While this disclosure describes in detail the use of the snap connector 400 in connection with the cap-bladder assembly 100, this disclosure is specifically intended not to be limited to this particular modality (e.g., a cap bladder assembly), but may be adapted for use with any syringe system or fluid path set having a discharge outlet 110 similar to that shown in FIGS. 4-15. The choice of a cap-bladder assembly 100 is exemplary for showing the connection aspects and features when using the snap connector 400 with the discharge outlet 110. Accordingly, the cap 102 may have a conical cap body 104 and a discharge outlet 110 that is representative of any typical syringe with a syringe barrel with an open proximal end, a conical shaped discharge area at its distal end, and a discharge outlet port or barrel extending from the conical shaped discharge area of the syringe. Moreover the terms "snap" or "snap luer" as used in this application are intended to be reflective of the operation of the connector 400 as it is connected to a discharge outlet 110 of any configuration and should not be deemed as limiting within this disclosure.

As shown, the discharge outlet 110 of the cap 102 includes a sidewall 111 extending between a distal end 112 and a proximal end 113 connected to the exterior of the cap body 104. The sidewall 111 may have a cylindrical or substantially cylindrical external shape and includes an inner surface that defines an internal passage 114. The internal passage 114 of the discharge outlet 110 is in fluid communication with the interior cavity 106, and thus the interior of the membrane portion 151 of the disc-shaped bladder 150, by way of a discharge orifice 108 extending through the cap body 104 from the internal surface 105 to the exterior of the cap body 104.

Figure 11A:
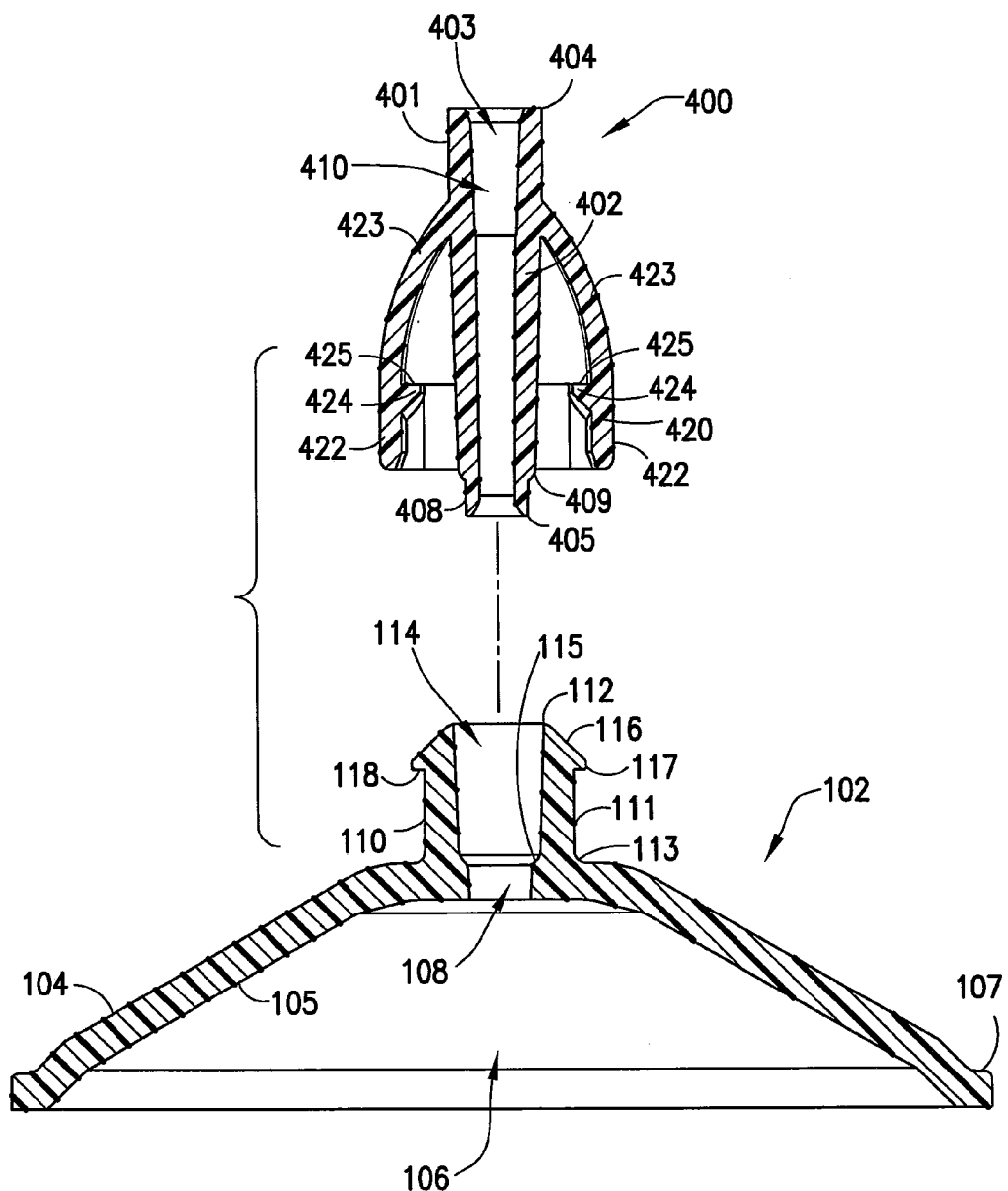
FIG. 11A is an exploded cross-sectional side view of the cap and the snap connector of FIG. 9.
Figure 11B:
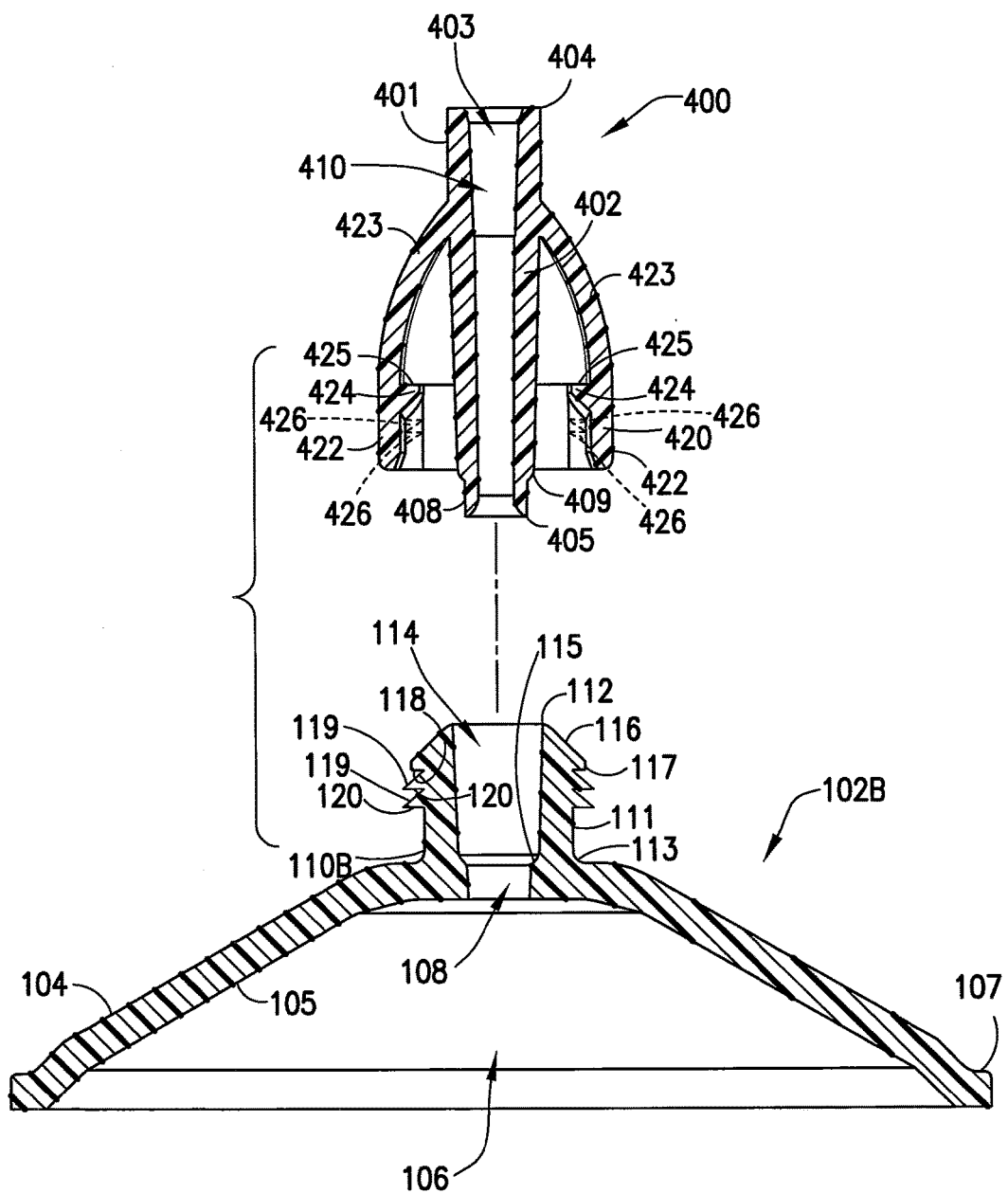
FIG. 11B is an exploded cross-sectional side view of a cap and snap connector in accordance with another embodiment of this disclosure.
Figure 11C:
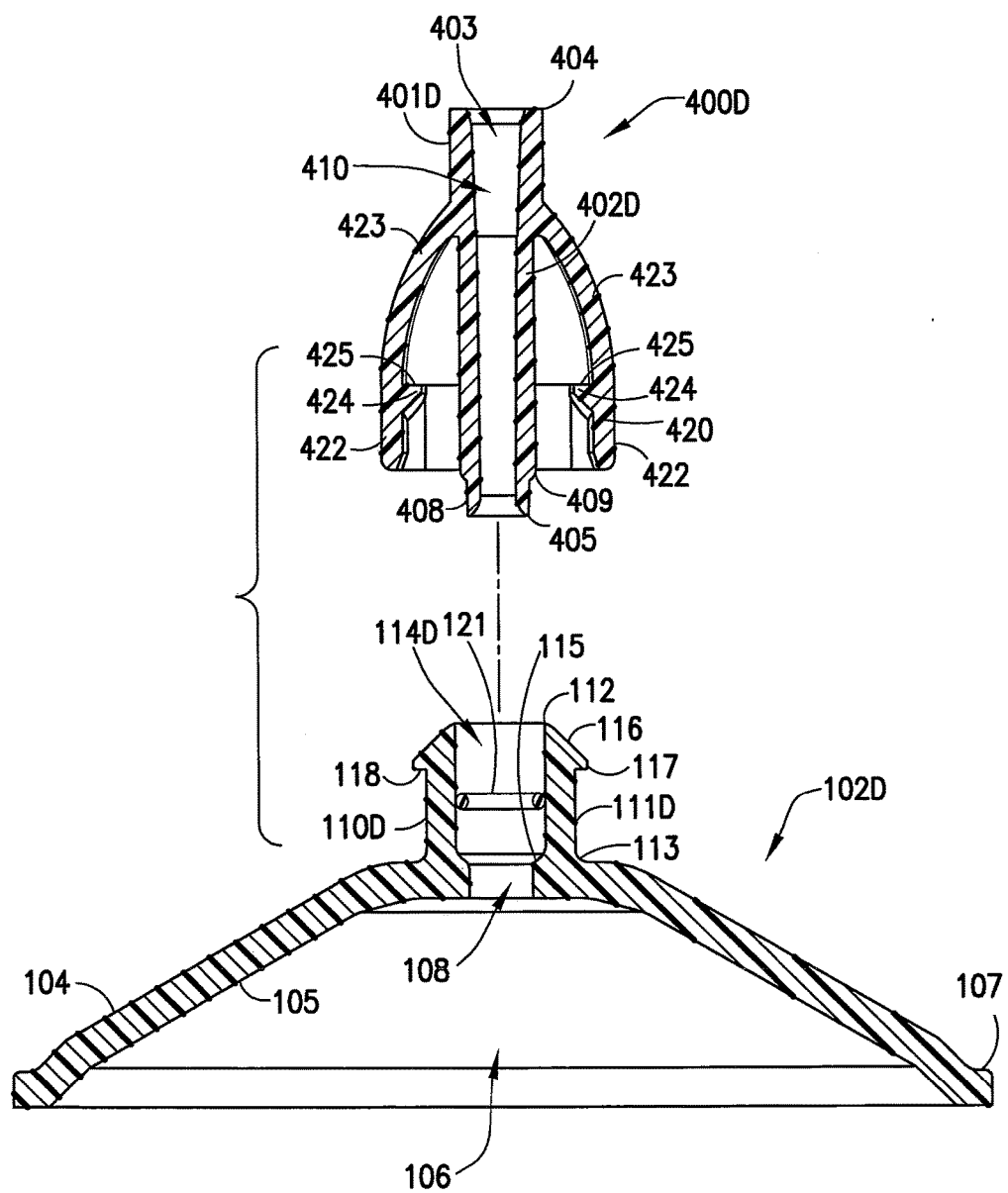
FIG. 11C is an exploded cross-sectional side view of a cap and snap connector in accordance with another embodiment of this disclosure
Figure 11D:
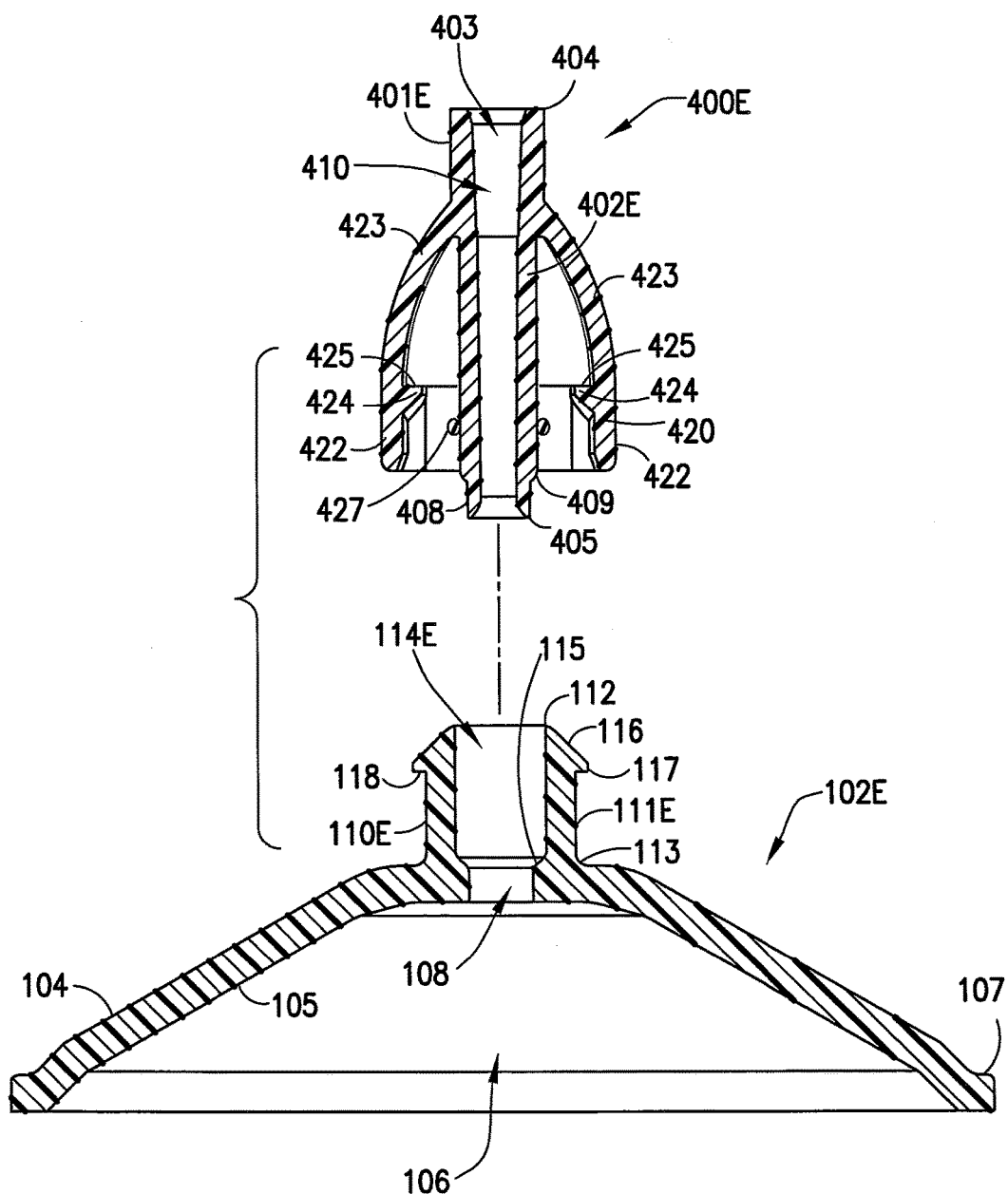
FIG. 11D is an exploded cross-sectional side view of a cap and snap connector in accordance with another embodiment of this disclosure.
Figure 12:
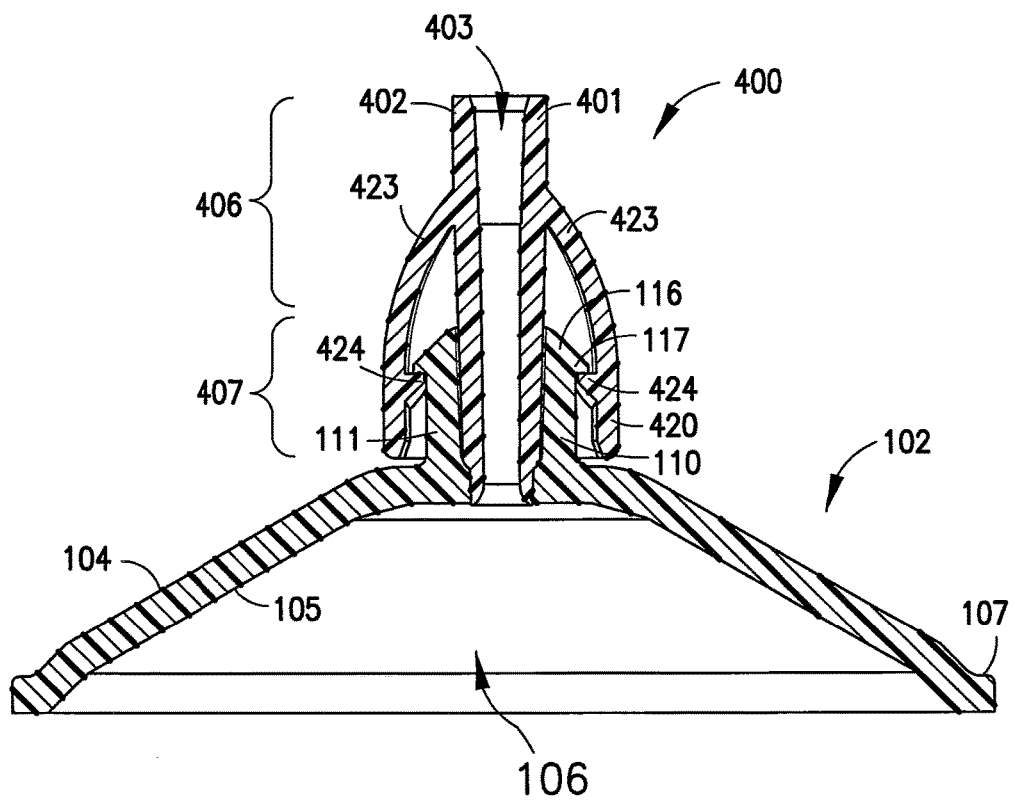
FIG. 12 is a cross-sectional side view of the cap and the snap connector of FIG. 9 when attached.
Figure 13:
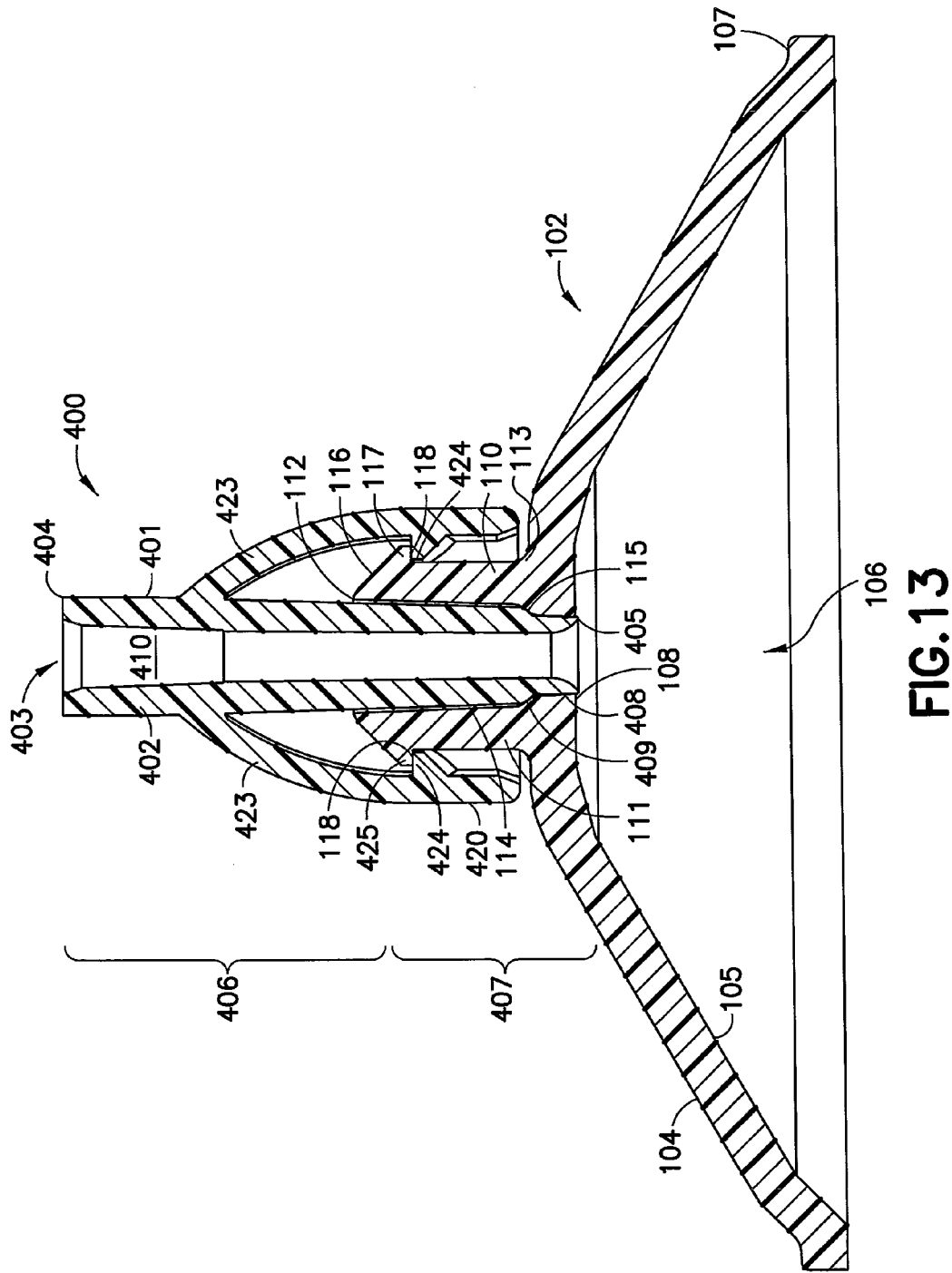
FIG. 13 is an enlarged cross-sectional side view of the cap and the snap connector of FIG. 9 when attached.

As shown in FIGS. 4-15, the snap connector 400 includes a central body 401, which has a sidewall 402 and is configured to be at least partially positioned within the internal passage 114 of the discharge outlet 110, and an annular connector portion 420, which is connected to the central body 401 and is configured to releasably engage the sidewall 111 of the discharge outlet 110. The sidewall 402 of the central body 401 has a cylindrical or substantially cylindrical shape and extends from a distal end 404 to a proximal end 405 and defines an internal channel 403 within the central body 401 that extends from the distal end 404 of the central body 401 to the proximal end 405 and is in fluid communication with the interior cavity 106 of the cap body 104 when the snap connector 400 is attached to the discharge outlet 110. The sidewall 402 of the central body 401 also defines a distal portion 406 (FIG. 12) of the central body 401 that extends beyond the distal end 112 of the discharge outlet 110 and a proximal portion 407 (FIG. 12) of the central body 401 that is positioned within the internal passage 114 of the discharge outlet 110 when the snap connector 400 is attached to the discharge outlet 110, as shown in FIGS. 10A, 12, and 13.

As shown in FIGS. 11A-13, the internal passage 114 of the discharge outlet 110 is inwardly tapering from the distal end 112 of the discharge outlet 110 towards the proximal end 113. A conical transition surface or internal shoulder 115 is also defined in the internal passage 114 at the proximal end 113 of the discharge outlet 110 where the internal passage 114 joins the discharge orifice 108 of the cap body 104 to place the internal passage 114 in fluid communication with the interior cavity 106 of the cap body 104. The sidewall 402 in at least the proximal portion 407 of the central body 401 of the snap connector 400 is also inwardly tapered such that the proximal portion 407 is contoured to correspond to the inwardly tapering shape of the internal passage 114 of the discharge outlet 110. The central body 401 of the snap connector 400 also includes a narrowed tip 408 defined at the proximal end 405 of the central body 401. The central body 401 and the narrowed tip 408 are configured such that the narrowed tip 408 extends into the discharge orifice 108 of the cap body 104 and terminates substantially flush with the internal surface 105 of the cap body 104 when the snap connector 400 is connected to the discharge outlet 110 such that fluid travels from the disc-shaped bladder 150 directly into the internal channel 403 of the central body 401. Additionally or alternatively, the narrowed tip 408 may be terminated substantially flush with the proximal end 113 of the discharge outlet 110. A conical flange or external shoulder 409 may also be defined in the sidewall 402 in the proximal portion 407 of the central body 401 to correspond to the contour of the transition surface 115 between the internal passage 114 of the discharge outlet 110 and the discharge orifice 108 of the cap body 104.

It is to be appreciated that the material of the cap body 104 and the sidewall 111 of the discharge outlet 110 forming the transition surface 115 may be of a nature such that the transition surface 115 is somewhat elastic and compresses when engaged by the external shoulder 409 of the sidewall 402 of the central body 401 of the snap connector 400. Alternatively or additionally, the sidewall 402 of the central body 401 of the snap connector 400 may be formed to be somewhat elastic and to compress when the transition surface 115 engages the external shoulder 409. In this manner, the elastic compressed engagement between the transition surface 115 and the external shoulder 409 formed when the snap connector 400 engages the discharge outlet 110 may create a type of spring release that serves to eject the central body 401 of the snap connector 400 from the central passage 114 of the discharge outlet 110 when the snap connector 400 is disengaged from the discharge outlet 110.

Further, with reference to FIGS. 11A-13 and 15, a portion of the internal channel 403 of the central body 401 of the snap connector 400 defines a female luer fitting 410 that is configured to releasably engage a tubing element 501 of a disposable fluid set 500, as shown in FIG. 15. The disposable fluid set 500, as shown in FIG. 15, may be associated with the bladder syringe 20 by joining this set 500 to the female luer fitting 410 defined in the snap connector 400 when the snap connector 400 is attached to the discharge outlet 110 of the cap 102. Alternatively, the disposable fluid set 500 may be provided as an integral part of the snap connector 400 or the distal portion 406 of the central body 401 of the snap connector 400 may be configured as a male luer fitting that may be inserted in a female luer fitting formed at the end of the tubing element 501. The disposable fluid set 500 may include one or more tubing elements 501 terminating in a container spike or another medical connector element 502 for placing the bladder syringe 20 in fluid communication with one or more bottles or bags containing desired injection fluids.

With reference to FIGS. 4-14, the connector portion of the snap connector 400 includes an annular connector portion in the form of an elliptical connector ring 420 that is connected to the central body 401 of the snap connector 400 and surrounds the proximal portion 407 of the central body 401. The elliptical connector ring 420 has two opposing major vertices 421 and two opposing minor vertices 422, and the elliptical connector ring 420 is connected to the distal portion 406 of the central body 401 by at least two radially and proximally extending curved arms 423 that extend between the distal portion 406 of the central body 401 and the minor vertices 422 of the elliptical connector ring 420. As shown in FIGS. 9-14, the sidewall 111 of the discharge outlet 110 includes a conical tip 116 defined at the distal end 112 of the discharge outlet 110. The conical tip 116 defines a flange 117 having a proximally facing abutment surface 118 that surrounds the sidewall 111 of the discharge outlet 110. The elliptical connector ring 420 also includes at least two inward radially-extending flanges 424 positioned at the minor vertices 422 of the elliptical connector ring 420. The inward radially-extending flanges 424 define distally facing abutment surfaces 425 that engage the mating abutment surface 118 of the flange 117 of the conical tip 116 of the discharge outlet 110 when the snap connector 400 is connected to the discharge outlet 110 in order to retain the connection between snap connector 400 and the discharge outlet 110. The mating abutment surfaces 118, 425 of the conical tip 116 and the inward radially-extending flanges 424 are configured such that they can become disengaged by pressing the major vertices 421 of the elliptical connector ring 420 towards each other. As shown in FIG. 14, pressing inward on the major vertices 421 of the elliptical retainer ring 420 in the direction of arrows A causes the minor vertices 422 to move radially outward in the direction of arrows B. In such a manner, the snap connector 400 can be disconnected and removed from the discharge outlet 110 of the cap 102.

With reference to FIG. 11B, in accordance with another embodiment of the disclosure, a cap 102B may be provided with a discharge outlet 110B having a sidewall 111 that defines at least one additional flange 119 having a proximally-facing abutment surface 120. In particular, the sidewall 111 may define two additional flanges 119, as shown, or perhaps as many as 3 or 4. The at least one additional flange 119 is defined proximally of the distal end flange 117 of the sidewall 111 of the discharge outlet 110B. As also shown in FIG. 11B, in like manner, the snap connector 400 may also include one or more additional flanges 426 (shown in phantom lines) positioned on the inside of the connector ring 420 at the minor vertices 422 proximally of the radially-extending flanges 424. These additional flanges 426 also include abutment surfaces suitable for engaging the abutment surface 118 of the distal end flange 117 or the abutment surfaces 120 of the additional flanges 119 disposed on the discharge outlet 110B. Providing the connector 400 and the discharge outlet 110B with multiple sets of mutually engageable flanges 117, 119, 424, 426 allows for variation in the size of the flanges, in particular the radial width/depth of the abutment surfaces and the steepness of the shape of the flanges 117, 119, 424, 426, which relates to holding strength. In other words, the size of the flanges needed to properly maintain the connection between the discharge outlet 110B and the connector 400 may be reduced if additional mutually engageable flanges 119, 426 are provided. Additionally, the additional flanges 119, 426 allow for variation in the axial connected position of the connector 400 with respect to the discharge outlet 110B, for example, to take up the axial travel due to tolerances of a luer connection as is further discussed below.

With reference to FIG. 11C, in accordance with another embodiment of the disclosure, a cap 102D may be provided with a discharge outlet 110D having a sidewall 111D that is formed straight defines an internal passage 114D. A sealing member or gasket 121 made from elastic material may be an O-ring simply inserted into the straight internal passage 114D or may be co-injection molded to be integrally formed with the interior of the sidewall 111D. The gasket 121 will engage a straight cylindrical sidewall 402D of the central body 401D of the connector 400D to ensure a sealing relationship between the discharge outlet 110D and the connector 400D. The gasket 121 may also be positioned within the internal passage 114D of the discharge outlet 110D such that it compresses during engagement with the central body 401D of the connector 400D. In this manner, the gasket 121 may also function in the manner of a spring to eject or push the central body 401D from the internal passage 114D when the connector ring 420 is disengaged from the discharge outlet 110D, as will be discussed in further detail below. In particular, the gasket 121 may be disposed at the proximal end 113 of the discharge outlet 110D against the internal shoulder 115 such that the external shoulder 409 of the connector 400D creates a 'butt' seal compressing the gasket 121 in the axial direction and providing a resisting force against the external shoulder 409 of the connector 400D that allows it to 'spring' upwards when the engagement between the connector ring 420 of the connector 400D and the discharge outlet 110D is released. Alternatively, the gasket 121 may be provided within the internal passage 114D along the interior surface of the sidewall 111D intermediately of the proximal end 113 and the distal end 112 of the discharge outlet 110D, which may further incorporate a mating surface or area (not shown) for the gasket 121 to bear against.

Alternatively, with reference to FIG. 11D, in accordance with another embodiment of the disclosure, a connector 400E may be formed with a sealing member or gasket 427 co-injection molded onto the exterior of a straight cylindrical sidewall 402E of the central body 401E. The gasket 427 will engage the straight internal sidewall 111E of the discharge outlet 110E of the cap 102E within the internal passage 114 to ensure a sealing relationship between the central body 401E of the connector 400E and the discharge outlet 110E. It is to be appreciated with respect to either of the embodiments of FIGS. 11C and 11D, the connection between the connector 400 and the discharge outlet 110 of the other embodiments of the present disclosure may be a type of luer connection formed with a 6% slope on both the connector 400 and the discharge outlet 110. Considering that the engagement between the connector 400 and the discharge outlet 110 is between two plastic elements, there is a 0.125 inch axial tolerance required between the connector 400 and the discharge outlet 110 that form the engagement. In certain applications, such a tolerance may be difficult to take up and still ensure a seal between the connector 400 and the discharge outlet 110. However, when the interior of the cylindrical sidewall 111D, 111E of the discharge outlet 110D, 110E and the exterior of the cylindrical sidewall 402D, 402E of the central body 401D, 401E of the connector 400D, 400E are formed straight, as described above, and a sealing member or gasket 121, 427 is co-injected with one or the other, then there is no required axial tolerance between the discharge outlet 110D, 110E and the connector 400D, 400E after the seal is achieved. Further axial travel of the discharge outlet 110D, 110E and the connector 400D, 400E with respect to each other does not affect the seal.

It is to be appreciated that the snap connector 400 may be integrally molded from a suitable flexible or elastic material, such as polyethylene, that is capable of flexing in the manner described above for connecting and disconnecting the snap connector 400 to the discharge outlet 110 of the cap 102 while also tolerating the stresses involved with pressurizing and de-pressurizing the disc-shaped bladder 150 and transmitting fluids to and from the bladder syringe 20 via the disposable fluid set 500 and the snap connector 400. It is also to be appreciated that the snap connector 400 and the discharge outlet 110 of the cap 102 may be formed in a variety of complementary configurations that allow for easy and efficient connection and disconnection of the snap connector 400 from the discharge outlet 110. Further, the snap connector 400, itself, may be of any suitable configuration. For instance, the connecting arms 423 may be straight or connect to other portions of the elliptical connector ring 420 than the minor vertices 422. Further, the elliptical connector ring 420 may instead have an oblong circular shape, a diamond shape, or some other shape whereby pressing inward on opposing portions of the ring 420 causes other portions of the ring 420 to separate.

With reference to FIGS. 1-15, in accordance with an embodiment of this disclosure, a method of releasably connecting a tubing element 501 of a disposable fluid set 500 to a bladder syringe 20 of a fluid delivery system 10 includes the steps of providing a bladder syringe 20 having a cylindrical body 30 and cap-bladder assembly 100, as described above with reference to FIGS. 1-3 and 9-14; providing a snap connector 400 as described above with reference to FIGS. 4-15; inserting the tubing element 501 into a portion 410 of the internal channel 403 of the central body 401 of the snap connector 400 to releasably connect the tubing element 501 to the central body 401; positioning a proximal portion 407 of the central body 401 of the snap connector 400 within the internal passage 114 of the discharge outlet 110 of the cap 102 such that the internal channel 403 of the central body 401 is in fluid communication with the interior cavity 106 of the cap body 104; and engaging the abutment surface 118 of the flange 117 of the conical tip 116 of the discharge outlet 110 with the abutment surfaces 425 of the inward radially-extending flanges 424 of the elliptical connector ring 420 to connect the snap connector 400 to the discharge outlet 110 of the cap 102. The method may include the additional step of pressing inward on the elliptical retainer ring 420 at the major vertices 421 to disengage the abutment surfaces 425 of the inward radially-extending flanges 424 from the abutment surface 118 of the flange 117 of the conical tip 116 of the discharge outlet 110 and disconnect the snap connector 400 from the discharge outlet 110.

Figure 10A:
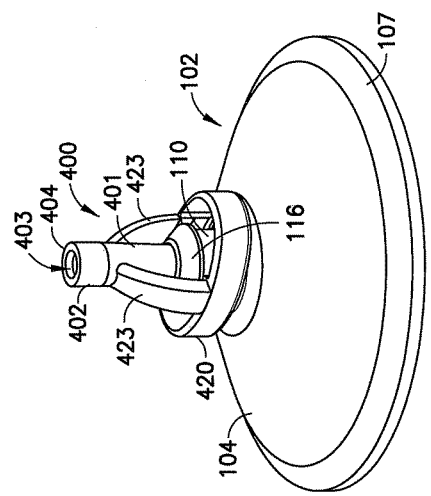
FIG. 10A is a perspective view of the cap and the snap connector of FIG. 9 when attached.
Figure 10B:
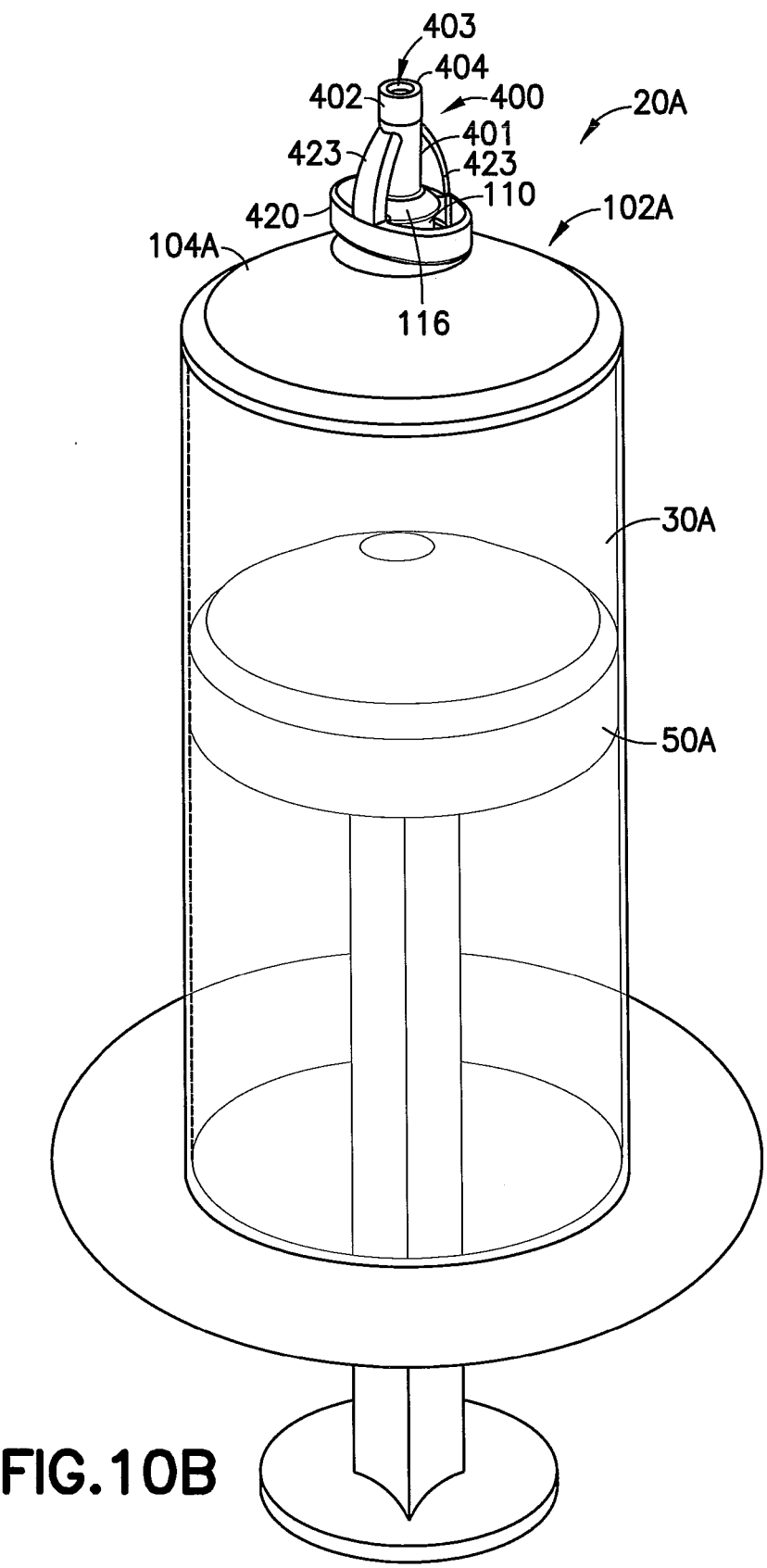
FIG. 10B is a perspective view of a syringe assembly incorporating the discharge outlet and snap connector of FIG. 9 in accordance with another embodiment of this disclosure.

As discussed above, the present invention is not limited to the use of the snap connector 400 and discharge outlet 110 on the above-detailed cap-bladder assembly 100 of the bladder syringe 20. For instance, with reference to FIG. 10B, the present invention is compatible with practically any syringe or fluid pump device configuration known to those having ordinary skill in the art. As shown in FIG. 10B, a basic syringe/fluid pump device 20A includes a cylindrical body or barrel 30A and a plunger assembly/pump actuator 50A having a plunger rod and plunger slidably disposed within the barrel 30A in a manner well known to those having ordinary skill in the art. A distal end 102A of the barrel 30A is formed with a conical distal wall or body 104A acting as the discharge area with the discharge outlet 110, as described above, extending distally from the conical body 104A. The snap connector 400, as described above, can be connected and disconnected from the discharge outlet 110 in accordance with the above-described embodiments. Accordingly, it is to be appreciated that the term "conical body" as used throughout this application encompasses not only a conical cap but also the typical conical end of a syringe body having a discharge outlet extending from the conical end.

Figure 16:
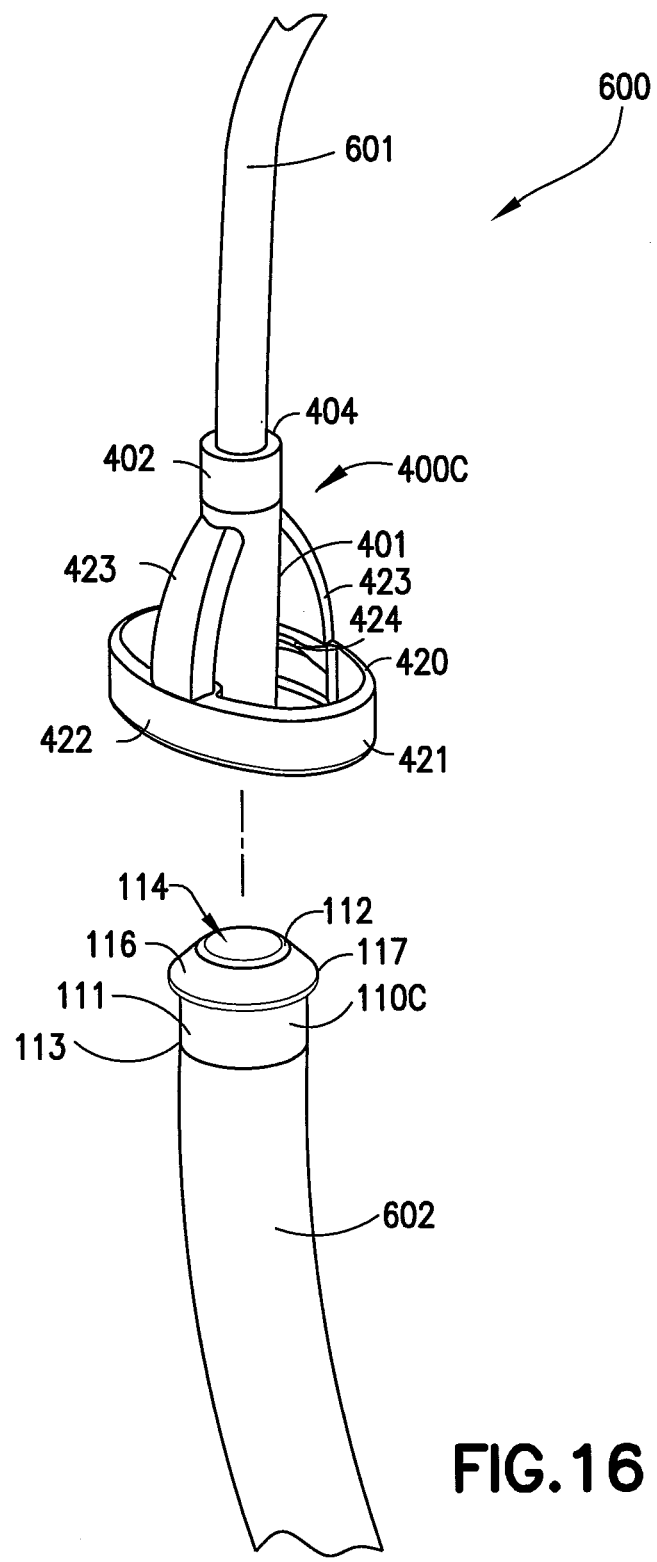
FIG. 16 is a perspective view of a connector assembly incorporating the discharge outlet and snap connector of FIG. 9 in accordance with another embodiment of this disclosure.

With reference to FIG. 16, a connector assembly 600 is shown in accordance with another embodiment of this disclosure. The connector assembly 600 includes a first connector element 110C that is configured in a similar manner as the discharge outlets 110, 110A, 110B discussed above, except that the first connector 110C is not necessarily associated with a cap or a distal end of a syringe, but may instead, by way of example, be positioned at the end of a tubing element 602. Alternatively, the first connector 110C may constitute a fluid flow inlet or outlet of any one of a number of different fluid injection devices that deliver a fluid to a patient for treatment or diagnostic purposes. Several examples of such devices are devices are described below. In particular, the first connector includes a sidewall 111 extending between a proximal end 113 and a distal end 112 and defining an internal passage 114 therebetween. A second connector element 400C is removably attached to the first connector element 110C. The second connector element 400C is a snap connector having the same configuration as the connector 400 discussed above with reference to the other embodiments. The second connector element 400C is positioned at the end of another tubing element 601. The second connector element 400C includes a central body 401 configured to be at least partially positioned within the internal passage 114 of the first connector element 110C. The central body 401 includes an annular connector portion/connector ring 420, to the central body 401. The annular connector portion 420 is configured to releasably engage an exterior of the sidewall 111 of the first connector element 110C when the second connector element 400C is attached to the first connector element 110C. The central body 401 defines an internal channel 403 (not shown in FIG. 16, see FIG. 11A as an example) within the central body 401 that is in fluid communication with the internal passage 114 of the first connector element 110C when the second connector element 400C is attached to the first connector element 110C. Accordingly, it is to be appreciated that the present disclosure is not limited to engagements between the connector 400 and a syringe 20, 20A, but may also be utilized when forming common connections between any tubing elements 601, 602 or between other similar fluid conducting components as may be envisioned by one having ordinary skill in the art. Further, it is to be appreciated that the first connector element 110C and the second connector element 400C of the connector assembly 600 may be formed in accordance with any of the above-detailed embodiments, including having multiple additional flanges 119 defined on the sidewall 111 of the first connector element and multiple additional flanges 426 defined on the annular connector portion/ring 420, as discussed above with reference to FIG. 11B.

In another aspect of the invention, the second/snap connector 400C may constitute a discharge outlet of a bellows member used as part of a bellows syringe and may be connected to a first connector 110C constituting a discharge outlet or a cap body of a bellows syringe, such as the bellows syringe disclosed in U.S. Provisional Application No. 61/636,049, filed on Apr. 20, 2012, and entitled "Bellows Syringe Fluid Delivery System", the disclosure of which is incorporated by reference herein in its entirety, now U.S. patent application Ser. No. 13/834,624, filed Mar. 15, 2013, which is also incorporated by reference herein in its entirety.

Alternatively, since the bellows member of such a syringe is a semi-rigid, self-supporting container with a discharge outlet, second connector 400C can attach directly to a first connector 110C constituting the discharge outlet of the bellows member/container.

In yet another aspect of the invention, the second connector 400C may be used in association with a first connector 110C that constitutes any one outlet or inlet or multiple outlets or inlets of a fluid pump device of the type disclosed in any one of International Application Nos. PCT/US2012/056364, filed on Sep. 20, 2012, PCT/US2012/056328, filed on Sep. 20, 2012, and PCT/US2012/056355, filed on Sep. 20, 2012, all of which are hereby incorporated by reference as if set forth herein in their entireties.

Details of a syringe and an associated powered fluid injection or delivery system with which the fluid connector 400 may be used may be found in U.S. patent application Ser. No. 09/982,518, filed on Oct. 18, 2001, now issued as U.S. Pat. No. 7,094,216 on Aug. 22, 2006 (hereinafter "the '216 patent"), and is assigned to the assignee of the present application, the disclosure of which is incorporated herein by reference in its entirety. Additional examples of syringes and fluid delivery systems with which the fluid connector 400 may be used are also disclosed in the following references: U.S. patent application Ser. No. 10/825,866, filed on Apr. 16, 2004, now issued U.S. Pat. No. 7,556,619 on Jul. 7, 2009 (hereinafter "the '619 patent"); U.S. Pat. No. 8,337,456 to Schriver et al., issued Dec. 25, 2012; U.S. Pat. No. 8,147,464 to Spohn et al., issued Apr. 3, 2012; U.S. patent application Ser. No. 11/004,670, now published as U.S. 2008/0086087 on Apr. 10, 2008; U.S. patent application Ser. No. 07/929,926, filed on Aug. 17, 1992, now issued as U.S. Pat. No. 5,383,858 on Jan. 24, 1995; and U.S. patent application Ser. No. 10/466,418, filed on Jul. 16, 2003, now issued as U.S. Pat. No. 7,462,166 on Dec. 9, 2008, each of which are assigned to the assignee of the present application and the disclosures of which are incorporated herein by reference in their entireties.

A suitable multi-syringe powered fluid injector disclosing syringes with which the fluid connector 400 may be used is described in U.S. patent application Ser. No. 13/386,765, filed on Jan. 24, 2012, which published as U.S. Patent Application Publication No. 2012/0123257, and is assigned to the assignee of the present application, the disclosure of which is incorporated herein by reference in its entirety. Other relevant multi-fluid delivery systems disclosing syringe with which the fluid connector 400 may be used are disclosed in U.S. patent application Ser. No. 10/159,592, filed on May 30, 2002 (published as U.S. 2004/0064041), and U.S. patent application Ser. No. 10/722,370, filed Nov. 25, 2003 (published as U.S. 2005/0113754), each of which are assigned to the assignee of the present application and the disclosures of which are incorporated herein by reference in their entireties.

An exemplary hand manifold with which the fluid connector 400 may be used is disclosed in U.S. patent application Ser. No. 13/755,883, filed Jan. 31, 2013, assigned to the assignee of the present application, the disclosure of which is incorporated herein by reference. Further, a suitable syringe with which the fluid connector 400 may be used may be found in United States Patent Application Publication No. 2009/0216192 to Schriver, et al., assigned to the assignee of the present application and the disclosure of which is incorporated herein by reference in its entirety.

While embodiments of a connector assembly for use with a syringe system, such as the bladder syringe system depicted in various figures of this disclosure, and methods of operation thereof were provided in the foregoing description, those skilled in the art may make modifications and alterations to these embodiments without departing from the scope and spirit of the invention. Accordingly, the foregoing description is intended to be illustrative rather than restrictive. The various embodiments described hereinabove are defined by the appended claims and all changes that fall within the meaning and the range of equivalency of the claims are to be embraced within their scope.

The invention claimed is:

1. A connector assembly for a fluid delivery system, the connector assembly comprising:
    a conical cap body defining a conical interior cavity and comprising a discharge outlet, the discharge outlet defining an internal passage in fluid communication with the conical interior cavity and comprising a discharge tip having a radially outward-extending flange; and
    a connector removably attachable to the discharge outlet, the connector comprising a central body having a distal end and a proximal end, the proximal end configured to be at least partially positioned within the internal passage of the discharge outlet when the connector is attached to the discharge outlet, and the connector comprising an annular connector ring connected to the central body and configured to releasably engage an exterior of the radially outward-extending flange on the discharge tip of the discharge outlet, the central body defining an internal channel within the central body that is in fluid communication with the conical interior cavity of the conical cap body when the connector is attached to the discharge outlet, the annular connector ring comprising:
        two major vertices;
        two minor vertices;
        at least two radially and proximally extending arms, each arm having a first end connected to the central body and a second end connected to one of the minor vertices of the annular connector ring; and
        at least two radially inward-extending flanges on the minor vertices releasably engaging the radially outward-extending flange on the discharge tip of the discharge outlet when the connector is attached to the discharge outlet and detachable from the radially outward-extending flange on the discharge tip of the discharge outlet by flexing the connector ring by pressing the major vertices inward toward the central body.

2. The connector assembly according to claim 1, wherein the central body of the connector defines a distal portion that extends beyond a distal end of the discharge outlet and a proximal portion positioned within the internal passage of the discharge outlet when the connector is attached to the discharge outlet.

3. The connector assembly according to claim 1, wherein the proximal end of the central body of the connector is contoured to correspond to a shape of the internal passage of the discharge outlet.

4. The connector assembly according to claim 1, wherein the central body includes a narrowed tip defined at the proximal end of the central body, the narrowed tip being configured to extend into the internal passage and terminate substantially flush with an interior surface of the conical cap body.

5. The connector assembly according to claim 1, wherein a portion of the internal channel in the central body defines a luer fitting connection.

6. The connector assembly according to claim 1, wherein the central body and the annular connector ring are integrally molded.

7. A fluid delivery system, comprising:
   a fluid pump device defining an interior cavity and comprising a discharge outlet, the discharge outlet defining an internal passage in fluid communication with the interior cavity and comprising a discharge tip having a flange; and
   a connector removably attachable to the discharge outlet, the connector comprising a central body having a distal end and a proximal end, the proximal end configured to be at least partially positioned within the internal passage of the discharge outlet when the connector is attached to the discharge outlet, and comprising a connector ring connected to the central body and configured to releasably engage the flange on the discharge tip of the discharge outlet, the central body defining an internal channel in fluid communication with the interior cavity of the fluid pump device when the connector is attached to the discharge outlet, the connector ring comprising:
      two major vertices;
      two minor vertices;
      at least two radially and proximally extending arms, each arm having a first end connected to the central body and a second end connected to one of the minor vertices of the connector ring; and
      at least two radially inward-extending flanges on the minor vertices releasably engaging the flange on the discharge tip of the discharge outlet when the connector is attached to the discharge outlet and detachable from the flange on the discharge tip of the discharge outlet by flexing the connector ring by pressing the major vertices inward toward the central body.

8. The fluid delivery system according to claim 7, wherein the central body of the connector defines a distal portion that extends beyond a distal end of the discharge outlet and a proximal portion that is positioned within the internal passage of the discharge outlet when the connector is attached to the fluid pump device.

9. The fluid delivery system according to claim 7, wherein the proximal end of the central body of the connector is contoured to correspond to a shape of the internal passage of the discharge outlet.

10. The fluid delivery system according to claim 7, wherein the central body includes a narrowed tip defined at the proximal end of the central body, the narrowed tip being configured to extend into the internal passage of the discharge outlet and terminate substantially flush with the interior cavity of the fluid pump device.

11. The fluid delivery system according to claim 7, wherein the flange on the discharge tip has a proximally-facing abutment surface, and
   wherein the at least two inward radially-extending flanges on the minor vertices of the connector ring engage the abutment surface on the flange on the discharge tip when the connector is connected to the discharge outlet.

12. The fluid delivery system according to claim 11, further comprising abutment surfaces on the at least two inward radially-extending flanges on the minor vertices of the connector ring that are configured to be disengaged from the proximally-facing abutment surface on the flange on the discharge tip by pressing the major vertices of the connector ring towards each other.

13. A connector removably attachable to a discharge outlet of a syringe, the connector comprising:
   a central body having a distal end and a proximal end, the proximal end configured to be at least partially positioned within an internal passage of the discharge outlet when the connector is attached to the discharge outlet, and the connector comprising an annular connector ring connected to the central body and configured to releasably engage an exterior of a flange on the discharge outlet, the central body defining an internal channel within the central body that is in fluid communication with a conical interior cavity of a conical cap body when the connector is attached to the discharge outlet, the annular connector ring comprising:
      two major vertices;
      two minor vertices;
      at least two radially and proximally extending arms, each arm having a first end connected to the central body and a second end connected to one of the minor vertices of the annular connector ring; and
      at least two radially inward-extending flanges on the minor vertices releasably engaging the flange on the discharge outlet when the connector is attached to the discharge outlet and detachable from the flange on the discharge outlet by flexing the annular connector ring by pressing the major vertices inward toward the central body.

* * * * *

UNITED STATES PATENT AND TRADEMARK OFFICE
CERTIFICATE OF CORRECTION

PATENT NO. : 9,814,871 B2  
APPLICATION NO. : 13/835522  
DATED : November 14, 2017  
INVENTOR(S) : Wlodarczyk et al.

Page 1 of 1

It is certified that error appears in the above-identified patent and that said Letters Patent is hereby corrected as shown below:

In the Specification

In Column 3, Line 43, delete "defusing" and insert -- defining --, therefor.

In Column 12, Line 43, delete "central passage" and insert -- internal passage --, therefor.

Signed and Sealed this  
Fifth Day of March, 2019

Andrei Iancu  
*Director of the United States Patent and Trademark Office*